(12) United States Patent
Vermeij

(10) Patent No.: US 7,662,390 B2
(45) Date of Patent: Feb. 16, 2010

(54) *LAWSONIA INTRACELLULARIS* SUBUNIT VACCINE

(75) Inventor: Paul Vermeij, St. Anthonis (NL)

(73) Assignee: Intarvet International B.V.

( * ) Notice: Subject to any disclaimer, the term of this patent is extended or adjusted under 35 U.S.C. 154(b) by 159 days.

(21) Appl. No.: 10/571,490

(22) PCT Filed: Sep. 8, 2004

(86) PCT No.: PCT/EP2004/009995

§ 371 (c)(1),
(2), (4) Date: Mar. 9, 2006

(87) PCT Pub. No.: WO2005/026200

PCT Pub. Date: Mar. 24, 2005

(65) Prior Publication Data

US 2006/0286118 A1    Dec. 21, 2006

(30) Foreign Application Priority Data

Sep. 12, 2003    (EP) .................................. 03077861

(51) Int. Cl.
*A61K 39/02* (2006.01)
(52) U.S. Cl. .................................................. 424/190.1
(58) Field of Classification Search ........................ None
See application file for complete search history.

(56) References Cited

U.S. PATENT DOCUMENTS 5,885,823 A    3/1999    Knittel et al.

FOREIGN PATENT DOCUMENTS

| EP | 1 219 711 A2 | 12/2000 |
|---|---|---|
| EP | 1 094 070 A2 | 4/2001 |
| WO | WO 00 69903 | 11/2000 |
| WO | WO 02 26250 A2 | 4/2002 |

OTHER PUBLICATIONS

McCluskey et al. (Infect. Immun., 70:2899-2907, 2002).*
Bowie et al. (Science, 1990, 247:1306-1310).*
Burgess et al. (J. of Cell Bio. 111:2129-2138, 1990).*
Lazar et al. (Molecular and Cellular Biology; 1988, 8:1247-1252).*
Bork (Genome Research, 2000,10:398-400).*
Cruse et al., Illustrated Dict. of Immunology, 2nd ed., CRC Press, 2003, p. 46, 166, 382.*
McGuinness et al. (Mol. Microbiol., 7:505-514, 1993).*
Moudallal et al. (EMBO Journal, 1:1005-1010, 1982).*
Lawson et al., J. Comp. Path., 122:77-100, 2000.*
Gebhart, C.J., et al. "Genomic Sequence Survey of *Lawsonia intracellularis*, the causative agent of proliferative. . ." Database EMBL, Oct. 24, 2002, EMBL accession No. BH795495.

* cited by examiner

*Primary Examiner*—Robert B Mondesi
*Assistant Examiner*—Brian J Gangle
(74) *Attorney, Agent, or Firm*—William M. Blackstone

(57) ABSTRACT

The present invention relates to nucleic acid sequences encoding novel *Lawsonia intracelluaris* proteins. It furthermore relates to DNA fragments, recombinant DNA molecules and live recombinant carriers comprising these sequences. Also it relates to host cells comprising such nucleic acid sequences, DNA fragments, recombinant DNA molecules and live recombinant carriers. Moreover, the invention relates to proteins encoded by these nucleotide sequences and to their use for the manufacturing of vaccines. The invention also relates to vaccines for combating *Lawsonia intracellulairs* infections and methods for the preparation thereof. Finally the invention relates to diagnostic tests for the detection of *Lawsonia intracellularis* DNA, the detection of *Lawsonia intracellularis* antigens and of antibodies against *Lawsonia intracellularis*.

3 Claims, 1 Drawing Sheet

LAWSONIA INTRACELLULARIS SUBUNIT VACCINE

Figure 1:
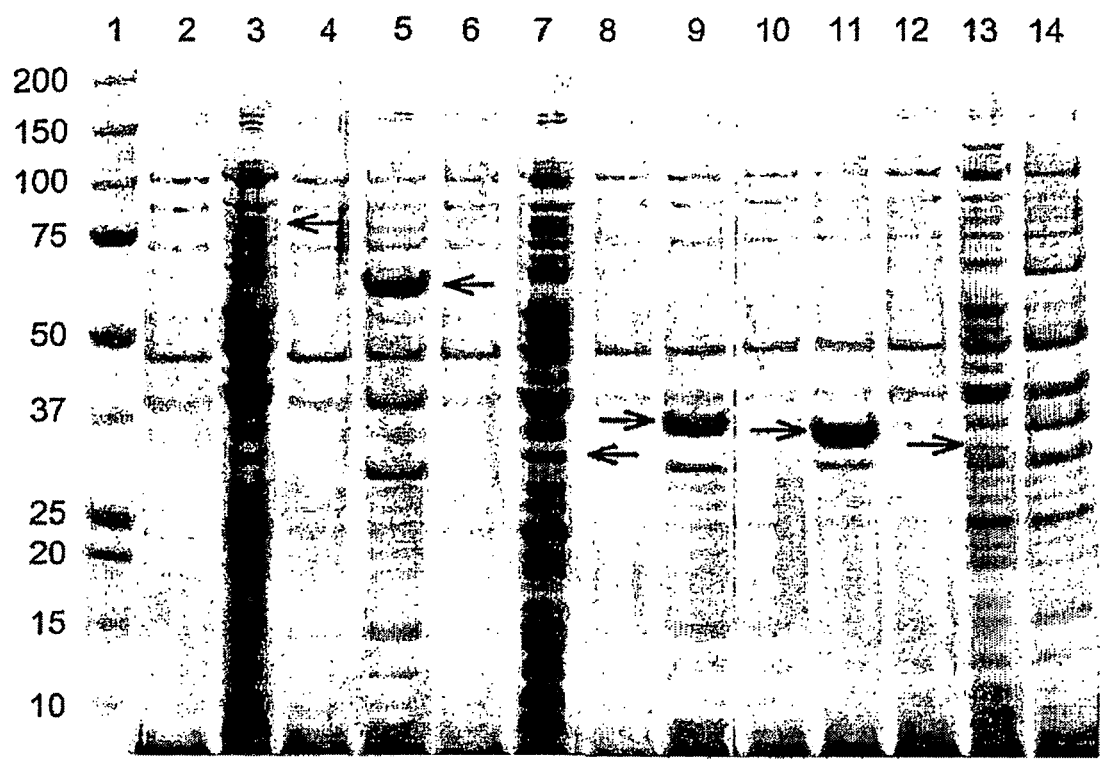

The material saved on two identical compact discs (COPY 1 and COPY 2) under the file name "Substitute Sequence Listing," created on Feb. 24, 2006, having a size of 54 bytes is hereby incorporated by reference.

Related Applications

This application is a national phase entry under 35 U.S.C. § 371 of International Application PCT/EP2004/009995 filed Sep. 8, 2004, which claims priority to EP Application 03077861.7 filed Sep. 12, 2003, all of which are incorporated herein by reference in their entirety.

The present invention relates to nucleic acid sequences encoding novel *Lawsonia intracellularis* proteins, to DNA fragments, recombinant DNA molecules and live recombinant carriers comprising these sequences, to host cells comprising such nucleic acid sequences, DNA fragments, recombinant DNA molecules and live recombinant carriers, to proteins encoded by these nucleotide sequences and to their use for the manufacturing of vaccines, to vaccines for combating *Lawsonia intracellularis* infections and methods for the preparation thereof and to diagnostic tests for the detection of *Lawsonia intracellularis* DNA, for the detection of *Lawsonia intracellularis* antigens and for the detection of antibodies against *Lawsonia intracellularis*.

Porcine proliferative enteropathy (PPE or PE) has become an important disease of the modern pig industry world-wide. The disease affects 15% to 50% of the growing herds and up to 30% of the individual animals in established problem herds. Today annual economical losses have been estimated US$ 5-10 in extra feed and facility time costs per affected pig. PPE is a group of chronic and acute conditions of widely differing clinical signs (death, pale and anaemic animals, watery, dark or bright red diarrhoea, depression, reduced appetite and reluctance to move, retarded growth and increased FCR). However there are two consistent features. The first, a pathological change only visible at necropsy, is a thickening of the small intestine and colon mucosa. The second is the occurrence of intracytoplasmatic small-curved bacteria in the enterocytes of the affected intestine. These bacteria have now been established as the etiological agent of PPE and have been name *Lawsonia intracellularis*.

Over the years *Lawsonia intracellularis* has been found to affect virtually all animals including monkeys, rabbits, ferrets, hamsters, fox, horses, and other animals as diverse as ostrich and emoe. *Lawsonia intracellularis* is a gram-negative, flagellated bacterium that multiplies in eukaryotic enterocytes only and no cell-free culture has been described. In order to persist and multiply in the cell *Lawsonia intracellularis* must penetrate dividing crypt cells. The bacterium associates with the cell membrane and quickly enters the enterocyte via an entry vacuole. This then rapidly breaks down (within 3 hours) and the bacteria flourish and multiply freely in the cytoplasm. The mechanisms by which the bacteria cause infected cells to fail to mature, continue to undergo mitosis and form hypoplastic crypt cells is not yet understood.

The current understanding of *Lawsonia intracellularis* infection, treatment and control of the disease has been hampered by the fact that *Lawsonia intracellularis* can not be cultivated in cell-free media. Although there are reports of successful co-culturing *Lawsonia intracellularis* in rat enterocytes this has not lead to the development of inactivated vaccines for combating *Lawsonia intracellularis*, although there clearly is a need for such vaccines.

It is an objective of the present invention to provide a vaccine for combating *Lawsonia intracellularis* infection.

It was surprisingly found now, that *Lawsonia intracellularis* produces six novel proteins that, alone or in combination, are capable of inducing protective immunity against *Lawsonia intracellularis*.

The novel proteins will be referred to as the 31.0 kD, 24.8 kD, 76.7 D, 56.8 kD, 28.8 kD and 31.4 kD protein.

The amino acid sequences of the novel proteins are presented in sequence identifiers SEQ ID NO: 2, 4, 6, 8, 10 and 12. The genes encoding these proteins have been sequenced and their nucleic acid sequence is shown in sequence identifiers SEQ ID NO: 1, 3, 5, 7, 9 and 11.

It is well-known in the art, that many different nucleic acid sequences can encode one and the same protein. This phenomenon is commonly known as wobble in the second and especially the third base of each triplet encoding an amino acid. This phenomenon can result in a heterology of about 30% for two nucleic acid sequences still encoding the same protein. Therefore, two nucleic acid sequences having a sequence homology of about 70% can still encode one and the same protein.

Thus, one embodiment relates to nucleic acid sequences encoding a *Lawsonia intracellularis* protein and to parts of that nucleic acid sequence that encode an immunogenic fragment of that protein, wherein those nucleic acid sequences or parts thereof have a level of homology with the nucleic acid sequence of SEQ ID NO: 1 of at least 90%.

Preferably, the nucleic acid sequence encoding this *Lawsonia intracellularis* protein or the part of said nucleic acid sequence has at least 92%, preferably 94%, more preferably 95% homology with the nucleic acid sequence of SEQ ID NO: 1. Even more preferred is a homology level of 98% or even 100%.

Another approach for deciding if a certain nucleic acid sequence is or is not a nucleic acid sequence according to the invention relates to the question if that certain nucleic acid sequence does hybridise under stringent conditions to the nucleotide sequence as depicted in SEQ ID NO: 1 (or in SEQ ID NO: 3, 5, 7, 9 or 11, see below).

If a nucleic acid sequence hybridises under stringent conditions to the nucleotide sequence as depicted in SEQ ID NO: 1, or of course as depicted in SEQ ID NO: 3, 5, 7, 9 and 11, it is considered to be a nucleic acid sequence according to the invention.

The definition of stringent conditions follows from the formula of Meinkoth and Wahl (1984. Hybridization of nucleic acids immobilized on solid supports. Anal. Biochem. 138: 267-284.)

$$Tm = [81.5° C. + 16.6(\log M) + 0.41(\% GC) - 0.61(\% \text{formamide}) - 500/L] - 1° C./1\% \text{ mismatch}$$

In this formula, M is molarity of monovalent cations; % GC is the percentage of guanosine and cytosine nucleotides in the DNA; L is the length of the hybrid in base pairs.

Stringent conditions are those conditions under which nucleic acid sequences or fragments thereof still hybridise, if they have a mismatch of 10% at the most, to the nucleic acid sequence as depicted in any of the SEQ ID NO: 1, 3, 5, 7, 9 or 11.

Also this embodiment relates to nucleic acid sequences encoding a *Lawsonia intracellularis* protein and to parts of that nucleic acid sequence that encode an immunogenic fragment of that protein, that have a level of homology with the nucleic acid sequence of SEQ ID NO: 3 of at least 90%.

Preferably, the nucleic acid sequence encoding this *Lawsonia intracellularis* protein or the part of said nucleic acid sequence has at least 92%, preferably 94%, more preferably 96% homology with the nucleic acid sequence of SEQ ID NO: 3. Even more preferred is a homology level of 98% or even 100%

Also this embodiment relates to nucleic acid sequences encoding a *Lawsonia intracellularis* protein and to parts of that nucleic acid sequence that encode an immunogenic fragment of that protein, that have a level of homology with the nucleic acid sequence of SEQ ID NO: 5 of at least 90%.

Preferably, the nucleic acid sequence encoding this *Lawsonia intracellularis* protein or the part of said nucleic acid sequence has at least 92%, preferably 94%, more preferably 96% homology with the nucleic acid sequence of SEQ ID NO: 5. Even more preferred is a homology level of 98% or even 100%

Also this embodiment relates to nucleic acid sequences encoding a *Lawsonia intracellularis* protein and to parts of that nucleic acid sequence that encode an immunogenic fragment of that protein, that have a level of homology with the nucleic acid sequence of SEQ ID NO: 7 of at least 90%.

Preferably, the nucleic acid sequence encoding this *Lawsonia intracellularis* protein or the part of said nucleic acid sequence has at least 92%, preferably 94%, more preferably 96% homology with the nucleic acid sequence of SEQ ID NO: 7. Even more preferred is a homology level of 98% or even 100%

Also this embodiment relates to nucleic acid sequences encoding a *Lawsonia intracellularis* protein and to parts of that nucleic acid sequence that encode an immunogenic fragment of that protein, that have a level of homology with the nucleic acid sequence of SEQ ID NO: 9 of at least 90%.

Preferably, the nucleic acid sequence encoding this *Lawsonia intracellularis* protein or the part of said nucleic acid sequence has at least 92%, preferably 94%, more preferably 96% homology with the nucleic acid sequence of SEQ ID NO: 9. Even more preferred is a homology level of 98% or even 100%

Also this embodiment relates to nucleic acid sequences encoding a *Lawsonia intracellularis* protein and to parts of that nucleic acid sequence that encode an immunogenic fragment of that protein, that have a level of homology with the nucleic acid sequence of SEQ ID NO: 11 of at least 90%.

Preferably, the nucleic acid sequence encoding this *Lawsonia intracellularis* protein or the part of said nucleic acid sequence has at least 92%, preferably 94%, more preferably 96% homology with the nucleic acid sequence of SEQ ID NO: 11. Even more preferred is a homology level of 98% or even 100%

Since the present invention discloses nucleic acid sequences encoding novel *Lawsonia intracellularis* proteins, it is now for the first time possible to obtain these proteins in sufficient quantities. This can e.g. be done by using expression systems to express the genes encoding the proteins.

Therefore, in a more preferred embodiment, the invention relates to DNA fragments comprising a nucleic acid sequence according to the invention. Such DNA fragments can e.g. be plasmids, into which a nucleic acid sequence according to the invention is cloned. Such DNA fragments are e.g. useful for enhancing the amount of DNA for use as a primer, as described below.

An essential requirement for the expression of the nucleic acid sequence is an adequate promoter functionally linked to the nucleic acid sequence, so that the nucleic acid sequence is under the control of the promoter. It is obvious to those skilled in the art that the choice of a promoter extends to any eukaryotic, prokaryotic or viral promoter capable of directing gene transcription in cells used as host cells for protein expression.

Therefore, an even more preferred form of this embodiment relates to a recombinant DNA molecule comprising a DNA fragment or a nucleic acid sequence according to the invention that is placed under the control of a functionally linked promoter. This can be obtained by means of e.g. standard molecular biology techniques. (Maniatis/Sambrook (Sambrook, J. Molecular cloning: a laboratory manual, 1989. ISBN 0-87969-309-6). Functionally linked promoters are promoters that are capable of controlling the transcription of the nucleic acid sequences to which they are linked.

Such a promoter can be a *Lawsonia* promoter e.g. the promoter involved in in vivo expression of the gene encoding the 31.0 kD, 24.8 kD, 76.7 D, 56.8 kD, 28.8 kD or 31.4 kD gene, provided that that promoter is functional in the cell used for expression. It can also be a heterologous promoter. When the host cells are bacteria, useful expression control sequences which may be used include the Trp promoter and operator (Goeddel, et al., Nucl. Acids Res., 8, 4057, 1980); the lac promoter and operator (Chang, et al., Nature, 275, 615, 1978); the outer membrane protein promoter (Nakamura, K. and Inouge, M., EMBO J., 1, 771-775, 1982); the bacteriophage lambda promoters and operators (Remaut, E. et al., Nucl. Acids Res., 11, 4677-4688, 1983); the α-amylase (*B. subtilis*) promoter and operator, termination sequences and other expression enhancement and control sequences compatible with the selected host cell.

When the host cell is yeast, useful expression control sequences include, e.g., α-mating factor. For insect cells the polyhedrin or p10 promoters of baculoviruses can be used (Smith, G. E. et al., Mol. Cell. Biol. 3, 2156-65, 1983). When the host cell is of mammalian origin illustrative useful expression control sequences include the SV-40 promoter (Berman, P. W. et al., Science, 222, 524-527, 1983) or the metallothionein promoter (Brinster, R. L., Nature, 296, 39-42, 1982) or a heat shock promoter (Voellmy et al., Proc. Natl. Acad. Sci. USA, 82, 4949-53, 1985).

Bacterial, yeast, fungal, insect and mammalian cell expression systems are very frequently used systems. Such systems are well-known in the art and generally available, e.g. commercially through Clontech Laboratories, Inc. 4030 Fabian Way, Palo Alto, Calif. 94303-4607, USA. Next to these expression systems, parasite-based expression systems are very attractive expression systems. Such systems are e.g. described in the French Patent Application with Publication number 2 714 074, and in U.S. NTIS Publication No U.S. Ser. No. 08/043,109 (Hoffman, S. and Rogers, W.: Public. Date 1 Dec. 1993).

A still even more preferred form of this embodiment of the invention relates to Live Recombinant Carriers (LRCs) comprising a nucleic acid sequence encoding the 31.0 kD, 24.8 kD, 76.7 D, 56.8 kD, 28.8 kD and 31.4 kD protein or an immunogenic fragment thereof according to the invention, a DNA fragment according to the invention or a recombinant DNA molecule according to the invention. Such carriers are e.g. bacteria and viruses. These LRCs are micro-organisms or viruses in which additional genetic information, in this case a nucleic acid sequence encoding the 31.0 kD, 24.8 kD, 76.7 D, 56.8 kD, 28.8 kD and 31.4 kD protein or an immunogenic fragment thereof according to the invention has been cloned. Animals infected with such LRCs will produce an immunogenic response not only against the immunogens of the carrier, but also against the immunogenic parts of the protein(s) for which the genetic code is additionally cloned into the LRC, e.g. the 31.0 kD, 24.8 kD, 76.7 D, 56.8 kD, 28.8 kD and 31.4 kD protein. As an example of bacterial LRCs, attenuated *Salmonella* strains known in the art can attractively be used.

Live recombinant carrier parasites have i.a. been described by Vermeulen, A. N. (Int. Journ. Parasitol. 28: 1121-1130 (1998))

Also, LRC viruses may be used as a way of transporting the nucleic acid sequence into a target cell. Live recombinant carrier viruses are also called vector viruses. Viruses often used as vectors are Vaccinia viruses (Panicali et al; Proc. Natl. Acad. Sci. USA, 79: 4927 (1982), Herpesviruses (E.P.A. 0473210A2), and Retroviruses (Valerio, D. et al; in Baum, S. J., Dicke, K. A., Lotzova, E. and Pluznik, D. H. (Eds.), Experimental Haematology today—1988. Springer Verlag, New York. pp. 92-99 (1989)).

The technique of in vivo homologous recombination, well-known in the art, can be used to introduce a recombinant nucleic acid sequence into the genome of a bacterium, parasite or virus of choice, capable of inducing expression of the inserted nucleic acid sequence according to the invention in the host animal.

Finally another form of this embodiment of the invention relates to a host cell comprising a nucleic acid sequence encoding a protein according to the invention, a DNA fragment comprising such a nucleic acid sequence or a recombinant DNA molecule comprising such a nucleic acid sequence under the control of a functionally linked promoter. This form also relates to a host cell containing a live recombinant carrier containing a nucleic acid molecule encoding a 31.0 kD, 24.8 kD, 76.7 D, 56.8 kD, 28.8 kD and 31.4 kD protein or a fragment thereof according to the invention.

A host cell may be a cell of bacterial origin, e.g. *Escherichia coli*, *Bacillus subtilis* and *Lactobacillus* species, in combination with bacteria-based plasmids as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses.

Another embodiment of the invention relates to the novel proteins and to immunogenic fragments thereof according to the invention.

The concept of immunogenic fragments will be defined below.

One form of this embodiment relates i.a. to *Lawsonia intracellularis* proteins that have an amino acid sequence that is at least 90% homologous to the amino acid sequence as depicted in SEQ ID NO: 2 and to immunogenic fragments of said protein.

In a preferred form, the embodiment relates to such *Lawsonia intracellularis* proteins that have a sequence homology of at least 92%, preferably 94%, more preferably 96% homology to the amino acid sequence as depicted in SEQ ID NO: 2 and to immunogenic fragments of such proteins.

Even more preferred is a homology level of 98% or even 100%.

Another form of this embodiment relates i.a. to *Lawsonia intracellularis* proteins that have an amino acid sequence that is at least 90% homologous to the amino acid sequence as depicted in SEQ ID NO: 4 and to immunogenic fragments of said protein.

A preferred form relates to such *Lawsonia intracellularis* proteins that have a sequence homology of at least 92%, preferably 94%, more preferably 96% homology to the amino acid sequence as depicted in SEQ ID NO: 4 and to immunogenic fragments of such proteins.

Even more preferred is a homology level of 98% or even 100%.

Another form of this embodiment relates i.a. to *Lawsonia intracellularis* proteins that have an amino acid sequence that is at least 90% homologous to the amino acid sequence as depicted in SEQ ID NO: 6 and to immunogenic fragments of said protein.

A preferred form relates to such *Lawsonia intracellularis* proteins that have a sequence homology of at least 92%, preferably 94%, more preferably 96% homology to the amino acid sequence as depicted in SEQ ID NO: 6 and to immunogenic fragments of such proteins.

Even more preferred is a homology level of 98% or even 100%.

Another form of this embodiment relates i.a. to *Lawsonia intracellularis* proteins that have an amino acid sequence that is at least 90% homologous to the amino acid sequence as depicted in SEQ ID NO: 8 and to immunogenic fragments of said protein.

A preferred form relates to such *Lawsonia intracellularis* proteins that have a sequence homology of at least 92%, preferably 94%, more preferably 96% homology to the amino acid sequence as depicted in SEQ ID NO: 8 and to immunogenic fragments of such proteins.

Even more preferred is a homology level of 98% or even 100%.

Another form of this embodiment relates i.a. to *Lawsonia intracellularis* proteins that have an amino acid sequence that is at least 90% homologous to the amino acid sequence as depicted in SEQ ID NO: 10 and to immunogenic fragments of said protein.

A preferred form relates to such *Lawsonia intracellularis* proteins that have a sequence homology of at least 92%, preferably 94%, more preferably 96% homology to the amino acid sequence as depicted in SEQ ID NO: 10 and to immunogenic fragments of such proteins.

Even more preferred is a homology level of 98% or even 100%.

Another form of this embodiment relates i.a. to *Lawsonia intracellularis* proteins that have an amino acid sequence that is at least 90% homologous to the amino acid sequence as depicted in SEQ ID NO: 12 and to immunogenic fragments of said protein.

A preferred form relates to such *Lawsonia intracellularis* proteins that have a sequence homology of at least 92%, preferably 94%, more preferably 96% homology to the amino acid sequence as depicted in SEQ ID NO: 12 and to immunogenic fragments of such proteins.

Even more preferred is a homology level of 98% or even 100%.

It will be understood that, for the particular proteins embraced herein, natural variations can exist between individual *Lawsonia intracellularis* strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/ Phe, Ala/Pro, Lys/Arg, Leu/Ile, Leu/Val and Ala/Glu. Based on this information, Lipman and Pearson developed a method for rapid and sensitive protein comparison (Science, 227, 1435-1441, 1985) and determining the functional similarity between homologous proteins. Such amino acid substitutions of the exemplary embodiments of this invention, as well as variations having deletions and/or insertions are within the scope of the invention as long as the resulting proteins retain their immune reactivity. This explains why *Lawsonia intracellularis* proteins according to the invention, when isolated from different field isolates, may have homology levels of about 90%, while still representing the same protein with the same immunological characteristics.

Those variations in the amino acid sequence of a certain protein according to the invention that still provide a protein capable of inducing an immune response against infection with *Lawsonia intracellularis* or at least against the clinical manifestations of the infection are considered as "not essentially influencing the immunogenicity".

When a protein is used for e.g. vaccination purposes or for raising antibodies, it is however not necessary to use the whole protein. It is also possible to use a fragment of that protein that is capable, as such or coupled to a carrier such as e.g. KLH, of inducing an immune response against that protein, a so-called immunogenic fragment. An "immunogenic fragment" is understood to be a fragment of the full-length protein that still has retained its capability to induce an immune response in the host, i.e. comprises a B- or T-cell epitope. At this moment, a variety of techniques is available to easily identify DNA fragments encoding antigenic fragments (determinants). The method described by Geysen et al (Patent Application WO 84/03564, Patent Application WO 86/06487, U.S. Pat. No. 4,833,092, Proc. Natl. Acad. Sci. 81: 3998-4002 (1984), J. 1 mm. Meth. 102, 259-274 (1987), the so-called PEPSCAN method is an easy to perform, quick and well-established method for the detection of epitopes; the immunologically important regions of the protein. The method is used world-wide and as such well-known to man skilled in the art. This (empirical) method is especially suitable for the detection of B-cell epitopes. Also, given the sequence of the gene encoding any protein, computer algorithms are able to designate specific protein fragments as the immunologically important epitopes on the asis of their sequential and/or structural agreement with epitopes that are now known. The determination of these regions is based on a combination of the hydrophilicity criteria according to Hopp and Woods (Proc. Natl. Acad. Sci. 78: 38248-3828 (1981)), and the secondary structure aspects according to Chou and Fasman (Advances in Enzymology 47: 45-148 (1987) and U.S. Pat. No. 4,554,101). T-cell epitopes can likewise be predicted from the sequence by computer with the aid of Berzofsky's amphiphilicity criterion (Science 235, 1059-1062 (1987) and U.S. Patent application NTIS U.S. Ser. No. 07/005,885). A condensed overview is found in: Shan Lu on common principles: Tibtech 9: 238-242 (1991), Good et al on Malaria epitopes; Science 235: 1059-1062 (1987), Lu for a review; Vaccine 10: 3-7 (1992), Berzowsky for HUV-epitopes; The FASEB Journal 5:2412-2418 (1991).

Therefore, one form of still another embodiment of the invention relates to vaccines capable of protecting pigs against *Lawsonia intracellularis* infection, that comprise one or more proteins or immunogenic fragments thereof, according to the invention as described above together with a pharmaceutically acceptable carrier.

Still another embodiment of the present invention relates to the proteins according to the invention for use in a vaccine.

Still another embodiment relates to the use of a protein according to the invention for the manufacturing of a vaccine for combating *Lawsonia intracellularis* infections.

One way of making a vaccine according to the invention is by biochemical purification of the proteins or immunogenic fragments thereof according to the invention from bacteria obtained through mucosal scrapings taken from the infected intestine wall. This is however a very time-consuming way of making the vaccine.

It is therefore much more convenient to use the expression products of the genes encoding the proteins or immunogenic fragments thereof according to the invention in vaccines. The nucleic acid sequences of the genes encoding the 31.0 kD, 24.8 kD, 76.7 D, 56.8 kD, 28.8 kD and 31.4 kD proteins are presented in the present invention.

Such vaccines based upon the expression products of these genes can easily be made by admixing one or more proteins according to the invention or immunogenic fragments thereof according to the invention with a pharmaceutically acceptable carrier as described below.

Alternatively, a vaccine according to the invention can comprise live recombinant carriers as described above, capable of expressing the proteins according to the invention or immunogenic fragments thereof according to the invention. Such vaccines, e.g. based upon a *Salmonella* carrier or a viral carrier infecting the enteric epithelium, or e.g. the respiratory epithelium have the advantage over subunit vaccines that they better mimic the natural way of infection of *Lawsonia intracellularis*. Moreover, their self-propagation is an advantage since only low amounts of the recombinant carrier are necessary for immunisation.

Vaccines described above all contribute to active vaccination, i.e. the host's immune system is triggered by one or more proteins according to the invention or immunogenic fragments thereof, to make antibodies against these proteins.

Alternatively, such antibodies can be raised in e.g. rabbits or can be obtained from antibody-producing cell lines as described below. Such antibodies can then be administered to the host animal. This method of vaccination, passive vaccination, is the vaccination of choice when an animal is already infected, and there is no time to allow the natural immune response to be triggered. It is also the preferred method for vaccinating immune-compromised animals. Administered antibodies against *Lawsonia intracellularis* can in these cases bind directly to the bacteria. This has the advantage that it immediately decreases or stops *Lawsonia intracellularis* growth.

Therefore, one other form of this embodiment of the invention relates to vaccines comprising antibodies against any of the six *Lawsonia intracellularis* proteins according to the invention.

Vaccines can also be based upon host cells as described above, that comprise the proteins or immunogenic fragments thereof according to the invention.

An alternative and efficient way of vaccination is direct vaccination with DNA encoding the relevant antigen. Direct vaccination with DNA encoding proteins has been successful for many different proteins. (As reviewed in e.g. Donnelly et al., The Immunologist 2: 20-26 (1993)).

This way of vaccination is very attractive for the vaccination of pigs against *Lawsonia intracellularis* infection.

Therefore, still other forms of this embodiment of the invention relate to vaccines comprising nucleic acid sequences encoding a protein according to the invention or immunogenic fragments thereof according to the invention, and to vaccines comprising DNA fragments that comprise such nucleic acid sequences.

Still other forms of this embodiment relate to vaccines comprising recombinant DNA molecules according to the invention.

DNA vaccines can easily be administered through intradermal application e.g. using a needle-less injector. This way of administration delivers the DNA-directly into the cells of the animal to be vaccinated. Amounts of DNA in the microgram range between 1 and 100 µg provide very good results.

In a further embodiment, the vaccine according to the present invention additionally comprises one or more antigens derived from other pig pathogenic organisms and viruses, or genetic information encoding such antigens.

Such organisms and viruses are preferably selected from the group of Pseudorabies virus, Porcine influenza virus, Porcine parvo virus, Transmissible gastro-enteritis virus, Rotavirus, *Escherichia coli, Erysipelothrix rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

All vaccines according to the present invention comprise a pharmaceutically acceptable carrier. A pharmaceutically acceptable carrier can be e.g. sterile water or a sterile physiological salt solution. In a more complex form the carrier can e.g. be a buffer.

Methods for the preparation of a vaccine comprise the admixing of a protein according to the invention, or an immunogenic fragment thereof, and a pharmaceutically acceptable carrier.

Vaccines according to the present invention may in a preferred presentation also contain an adjuvant. Adjuvants in general comprise substances that boost the immune response of the host in a non-specific manner. A number of different adjuvants are known in the art. Examples of adjuvants are Freunds Complete and Incomplete adjuvant, vitamin E, non-ionic block polymers, muramyldipeptides, Quill A®, mineral oil e.g. Bayol® or Markol®, vegetable oil, and Carbopol® (a homopolymer), or Diluvac® Forte.

The vaccine may also comprise a so-called "vehicle". A vehicle is a compound to which the polypeptide adheres, without being covalently bound to it. Often used vehicle compounds are e.g. aluminium hydroxide, -phosphate or -oxide, silica, Kaolin, and Bentonite.

A special form of such a vehicle, in which the antigen is partially embedded in the vehicle, is the so-called ISCOM (EP 109.942, EP 180.564, EP 242.380)

In addition, the vaccine may comprise one or more suitable surface-active compounds or emulsifiers, e.g. Span or Tween.

Often, the vaccine is mixed with stabilisers, e.g. to protect degradation-prone polypeptides from being degraded, to enhance the shelf-life of the vaccine, or to improve freeze-drying efficiency. Useful stabilisers are i.a. SPGA (Bovamik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent.

It goes without saying, that other ways of adjuvating, adding vehicle compounds or diluents, emulsifying or stabilising a polypeptide are also embodied in the present invention.

Vaccines according to the invention can very suitably be administered in amounts ranging between 1 and 100 micrograms, although smaller doses can in principle be used. A dose exceeding 100 micrograms will, although immunologically very suitable, be less attractive for commercial reasons.

Vaccines based upon live attenuated recombinant carriers, such as the LRC-viruses and bacteria described above can be administered in much lower doses, because they multiply themselves during the infection. Therefore, very suitable amounts would range between $10^3$ and $10^9$ CFU/PFU for respectively bacteria and viruses.

Many ways of administration can be applied. Oral application is a very attractive way of administration, because the infection is an infection of the digestive tract. A preferred way of oral administration is the packaging of the vaccine in capsules, known and frequently used in the art, that only disintegrate after they have passed the highly acidic environment of the stomach. Also, the vaccine could be mixed with compounds known in the art for temporarily enhancing the pH of the stomach.

Systemic application is also suitable, e.g. by intramuscular application of the vaccine. If this route is followed, standard procedures known in the art for systemic application are well-suited.

From a point of view of protection against disease, a quick and correct diagnosis of *Lawsonia intracellularis* infection is important.

Therefore it is another objective of this invention to provide diagnostic tools suitable for the detection of *Lawsonia intracellularis* infection.

A diagnostic test for the detection of *Lawsonia intracellularis* is e.g. based upon the reaction of bacterial DNA isolated from the animal to be tested, with specific probes or PCR-primers based upon the coding sequence of the gene encoding the 31.0 kD, 24.8 kD, 76.7 D, 56.8 kD, 28.8 kD and 31.4 kD protein. If *Lawsonia intracellularis* DNA is present in the animal, this will e.g. specifically bind to specific PCR-primers and will subsequently become amplified in PCR-reaction. The PCR-reaction product can then easily be detected in DNA gel electrophoresis.

The DNA can most easily be isolated from the microorganisms present in swabs taken from the digestive tract of the animal to be tested. Standard PCR-textbooks give methods for determining the length of the primers for selective PCR-reactions with *Lawsonia intracellularis* DNA. Primers with a nucleotide sequence of at least 12 nucleotides are frequently used, but primers of more than 15, more preferably 18 nucleotides are somewhat more selective. Especially primers with a length of at least 20, preferably at least 30 nucleotides are very generally applicable. PCR-techniques are extensively described in (Dieffenbach & Dreksler; PCR primers, a laboratory manual. ISBN 0-87969-447-5 (1995)).

Nucleic acid sequences encoding a *Lawsonia intracellularis* protein or parts of those nucleic acid sequences having a length of at least 12, preferably 15, more preferably 18, even more preferably 20, 22, 25, 30, 35 or 40 nucleotides in that order of preference, wherein the nucleic acid sequences or parts hereof have at least 90% homology with the nucleic acid sequence as depicted in SEQ ID NO: 1 or 3. Are therefore also part of the invention. Such nucleic acid sequences can be used as primers in PCR-reactions in order to enhance the amount of DNA that they encode. This allows the quick amplification of specific nucleotide sequences for use as a diagnostic tool for e.g. the detection of Lawsonia in tissue as indicated above.

Another DNA-based test is based upon growth of bacterial material obtained from the swab, followed by classical DNA purification followed by classical hybridisation with radioactively or colour-labelled 31.0 kD, 24.8 kD, 76.7 D, 56.8 kD, 28.8 kD and 31.4 kD protein-specific DNA-fragments. Both PCR-reactions and hybridisation reactions are well-known in the art and are i.a. described in Maniatis/Sambrook (Sambrook, J. et al. Molecular cloning: a laboratory manual. ISBN 0-87969-309-6).

Thus, one embodiment of the invention relates to a diagnostic test for the detection of *Lawsonia intracellularis* DNA. Such a test comprises a nucleic acid sequence according to the invention or a fragment thereof that is specific for the DNA encoding the 31.0 kD, 24.8 kD, 76.7 D, 56.8 kD, 28.8 kD and 31.4 kD protein. A fragment that is specific for that DNA is understood to be a fragment that, under comparable conditions, binds better to the *Lawsonia intracellularis* DNA than to DNA of other bacteria, due to higher homology with the *Lawsonia intracellularis* DNA, e.g. a primer of at least 12 nucleotides as described above.

A diagnostic test for the detection of *Lawsonia intracellularis* antibodies in sera can be e.g. a simple standard sandwich-ELISA-test in which 31.0 kD, 24.8 kD, 76.7 D, 56.8 kD, 28.8 kD and 31.4 kD protein or antigenic fragments thereof according to the invention are coated to the wall of the wells of an ELISA-plate. A method for the detection of such antibodies is e.g. incubation of 31.0 kD, 24.8 kD, 76.7 D, 56.8 kD, 28.8 kD and 31.4 kD protein or antigenic fragments thereof with serum from mammals to be tested, followed by e.g. incubation with a labelled antibody against the relevant mammalian antibody. A colour reaction can then reveal the presence or absence of antibodies against *Lawsonia intracellularis*. Another example of a diagnostic test system is e.g. the incubation of a Western blot comprising the 31.0 kD, 24.8 kD, 76.7 D, 56.8 kD, 28.8 kD and 31.4 kD protein or an antigenic fragment thereof according to the invention, with serum of mammals to be tested, followed by analysis of the blot.

Thus, another embodiment of the present invention relates to diagnostic tests for the detection of antibodies against *Lawsonia intracellularis*. Such tests comprise a protein or a fragment thereof according to the invention.

Also, the invention relates to methods for the detection in serum of antibodies against Lawsonia intracellularis, in which the method comprises the incubation of serum with the 31.0 kD, 24.8 kD, 76.7 D, 56.8 kD, 28.8 kD and 31.4 kD protein or antigenic fragments thereof according to the invention.

A diagnostic test based upon the detection of antigenic material of the specific 31.0 kD, 24.8 kD, 76.7 D, 56.8 kD, 28.8 kD and 31.4 kD proteins of *Lawsonia intracellularis* antigens and therefore suitable for the detection of *Lawsonia intracellularis* infection can e.g. also be a standard ELISA test. In one example of such a test the walls of the wells of an ELISA plate are coated with antibodies directed against the 31.0 kD, 24.8 kD, 76.7 D, 56.8 kD, 28.8 kD and 31.4 kD protein. After incubation with the material to be tested, labelled anti-*Lawsonia intracellularis* antibodies are added to the wells. A colour reaction then reveals the presence of antigenic material from *Lawsonia intracellularis*. Therefore, still another embodiment of the present invention relates to diagnostic tests for the detection of antigenic material of *Lawsonia intracellularis*. Such tests comprise antibodies against a protein or a fragment thereof according to the invention.

The polypeptides or immunogenic fragments thereof according to the invention expressed as characterised above can be used to produce antibodies, which may be polyclonal, monospecific or monoclonal (or derivatives thereof). If polyclonal antibodies are desired, techniques for producing and processing polyclonal sera are well-known in the art (e.g. Mayer and Walter, eds. *Immunochemical Methods in Cell and Molecular Biology*, Academic Press, London, 1987).

Monoclonal antibodies, reactive against the polypeptide according to the invention (or variants or fragments thereof) according to the present invention, can be prepared by immunising inbred mice by techniques also known in the art (Kohler and Milstein, *Nature,* 256, 495-497, 1975).

Methods for large-scale production of antibodies according to the invention are also known in the art. Such methods rely on the cloning of (fragments of) the genetic information encoding the protein according to the invention in a filamentous phage for phage display. Such techniques are described in review papers by Cortese, R. et al, (1994) in *Trends Biotechn.* 12: 262-267., by Clackson, T. & Wells, J.A. (1994) in *Trends Biotechn.* 12: 173-183, by Marks, J.D. et al., (1992) in J. Biol. Chem. 267: 16007-16010, by Winter, G. et al., (1994) in Annu. Rev. Immunol. 12: 433-455, and by Little, M. et al., (1994) Biotechn. Adv. 12: 539-555. The phages are subsequently used to screen camelid expression libraries expressing camelid heavy chain antibodies. (Muyldermans, S. and Lauwereys, M., Journ. Molec. Recogn. 12: 131-140 (1999) and Ghahroudi, M. A. et al., FEBS Letters 414: 512-526 (1997)). Cells from the library that express the desired antibodies can be replicated and subsequently be used for large scale expression of antibodies.

Still another embodiment of the invention relates to methods for the detection of antigenic material from *Lawsonia intracellularis* in which the method comprises the incubation of serum, tissue of body fluids with antibodies against the 31.0 kD, 24.8 kD, 76.7 D, 56.8 kD, 28.8 kD and 31.4 kD protein or an antigenic fragment thereof according to the invention.

Finally, an embodiment of the invention relates to nucleic acid sequences encoding a *Lawsonia intracellularis* protein or parts of those nucleic acid sequences having a length, wherein the nucleic acid sequences or parts hereof have at least 90% homology with the nucleic acid sequence as depicted in SEQ ID NO: 1, 3, 5, 7, 9 or 11. Such nucleic acid sequences can be used as primers in PCR-reactions in order to enhance the amount of DNA that they encode. This allows the quick amplification of specific nucleotide sequences for use as a diagnostic tool for e.g. the detection of *Lawsonia* in tissue as indicated above.

EXAMPLES

Example 1

Isolation of *L. intracellularis* from Infected Porcine Ilea.

*L. intracellularis* infected ilea, confirmed by histopathology and acid-fast Ziehl-Neelsen staining, were collected from pigs died with PE, and stored at −80° C. After thawing L. intracellularis bacteria were isolated from mucosal scrapings taken from the infected intestinal wall. The ileal scrapings were homogenized repeatedly in PBS in an omnimixer to release the intracellular bacteria as described by Lawson et al. (Vet. Microbiol. 10: 303-323 (1985)). Supernatant obtained after low-speed centrifugation to remove cell debris was filtered through 5.0, 3.0, 1.2, and 0.8 µm filters (Millipore). The filtrate was subsequently centrifuged at 8000 g for 30 min, giving a small pellet of *L. intracellularis* bacteria. These bacteria were further purified using a Percoll gradient. The identity of the purified bacteria was assessed by PCR (Jones et al., J. Clin. Microbiol. 31: 2611-2615 (1993)) whereas purity of the isolated bacteria (>95%) was assessed by phase contrast microscopy to reveal any contaminating bacteria or gut debris present.

Bacterial Strains and Plasmids

*E. coli* host strain BL21star(DE3) containing vector pLysSrare and plasmid pET22b were purchased from Novagen (Madison, Wis., USA. pET-HIS1 (1) was constructed as described in Schaller et al., Microbiology 145: 2105-2116 (1999). *E. coli* strain TOP10F' was purchased from Invitrogen (Groningen, the Netherlands). Stocks of all bacterial strains, containing 30% glycerol, were stored at −70° C.

*Lawsonia intracellularis* cells were isolated from infected ileal material as described above.

Culture Media, Buffers and Antibiotics

Luria Bertani broth (LB) were prepared according to standard procedures. LB plates were prepared by melting LB medium+1.5% agar in a microwave oven according to standard procedures. Plates were poured after cooling the solution down to 45° C., and if needed addition of ampicillin (ACS-Dophar, Raamsdonksveer, the Netherlands). Isopropyl-β-D-thiogalactopyranoside (IPTG) was purchased from Biosynth Ag (Staad, Switzerland).

PCR Amplification

PCR amplification was performed using a Geneamp 9700 PCR system (Applied Biosystems, Calif., USA). The PCR was performed with the Expand High Fidelity PCR System (Roche Diagnostics GmbH, Mannheim, Germany). The PCR mixture contained 52 U/ml Expand High Fidelity Enzyme Mix, Expand HF buffer with 2.5 mM $MgCl_2$, 16 mM dNTPs (Promega, Wisconsin, USA), 20 pmoles of primers and 15 ng chromosomal DNA of *Lawsonia intracellularis* as template. All primers used for amplification of DNA are listed in table 1.

DNA Isolation

In order to obtain highly purified *Lawsonia* chromosomal DNA, DNA was prepared using a Biorad chromosomal DNA isolation kit (Biorad, Veenendaal, the Netherlands) according to manufacturers instructions.

DNA Sequencing

DNA was sequenced on an ABI 310 automated sequencer (Perkin Elmer, Calif., USA). The sequence mixture contained: 100 ng PCR product, 2 µl terminator ready reaction mix (Perkin Elmer, Calif., USA), 2.4 pmoles of primer, 6 µl of buffer (200 mM Tris-HCl, pH8.5; 5 mM $MgCl_2$) and aqua dest up to 20 µl. This mixture was cycled on a Geneamp 9700. The program was composed of 25 cycles with 10 seconds 96° C., 5 seconds 50° C. and 2 minutes 60° C. The cycle sequence products were purified with Dye-Ex columns (Qiagen Inc., Calif., USA) according to manufacturers instructions and run on the ABI 310 automated sequencer. Sequence results were collected using ABI 310 Collection Software version 1.0.4 (Perkin Elmer, Calif., USA) and analysed with Sequence Analysis version 3.1 (Perkin Elmer, Calif., USA). Alignments were made using Sequence Navigator version 1.0.1 (Perkin Elmer, Calif., USA). Sequence analysis was performed using the Sequencer 4.1.4 (GeneCodes Ann Arbor, Calif., USA)

Ligation and Transformation.

Ligations were performed in a 1× ligation buffer with 1 unit of ligation enzyme (Gibco BRL Life Technologies Inc., USA) at 16° C. overnight. 1 µl of the ligation reaction was transformed to *E. coli* competent cells by heat shock. The BL21 star(DE3) *E. coli* competent cells and the TOP10F' *E. coli* competent cells were made competent by a method of Maniatis/Sambrook using buffers TFB1 (30 mM KOAc, 100 mM RbCl, 10 mM $CaCl_2$, 50 mM $MnCl_2$, 15% glycerol) and TFB2 (10 mM RbCl, 75 mM $CaCl_2$, 10 mM MES, 15% glycerol). After 1 hour of recovery in SOC-medium supplemented with 10 mM $MgSO_4$ and 20 mM glucose at 37° C., the cells were plated on LB plates with the appropriate antibiotics.

Expression of 10×HIS Fusion Proteins

*E. coli* strain BL21star(DE3) containing pLysSrare and the expression vector was grown overnight at 37° C. at 200 rpm in 5 ml LB with ampicillin. The overnight culture was diluted 1:100 in 50 ml LB with ampicillin. This culture was grown under the same conditions until the $OD_{600}$ reached 0.5, measured on a NovaspecII spectophotometer (Pharmacia, Woerden, the Netherlands). At this point (t=0) the culture was induced with IPTG to a final concentration of 1 mM and continued to grow for a subsequent 3 hours (t=3). 100 µl samples were taken for analysis. *E. coli* strain BL21star(DE3) containing pLysSrare was grown and induced under the same conditions and samples were taken as a negative control. The samples were analyzed by SDS page, followed by a Coomassie Brilliant Blue staining as described below. The remaining culture was centrifuged at 5,000 rpm and the pellet was stored at −20° C. until further use.

Polyacrylamide Gel Electrophoresis and Western Blotting

SDS-PAGE was performed using 4-12% Bis-Tris gels from the NuPAGE electrophoresis system (Novex, San Diego, USA). Before separation the samples were boiled for 5 minutes with sample buffer (sample:buffer=2:1) in the presence of β-mercapto ethanol. The gels were stained with Coomassie Brilliant Blue or blotted onto Immobulon-P-membrane (Millipore, Bedford, USA) by standard semi-dry Western blotting procedures. Chicken anti-Lawsonia polyclonal serum was raised against a whole cell preparation in n-GNE (water:oil=45:55). Serum E2-839 was obtained from a pig that had developed clinical signs and post-mortem lesions typical for *L. intracellularis* infection. The sera were pre-adsorbed using an equal volume crude cell extracts from BL21star(DE3) containing vector pLysSrare at 4° C. for 4 hours.

TABLE 1

Primers used for the amplification and cloning of the *Lawsonia intracellularis* genes.

| gene | Forward primer | | PCR product size | Reverse primer | | PCR product size |
|---|---|---|---|---|---|---|
| 11 | CATGCCATGGATAGT AATAATGATTCAATG ATTA | <210> SEQ ID NO: 13<br><211> 34<br><212> DNA<br><213> Lawsonia | 34 bp | CGCGGATCCTTATTT TGGAGATGTTGACA | <210> SEQ ID NO: 14<br><211> 29<br><212> DNA<br><213> Lawsonia | 29 bp |

TABLE 1-continued

Primers used for the amplification and cloning of the *Lawsonia intracellularis* genes.

| gene | Forward primer | | PCR product size | Reverse primer | | PCR product size |
|---|---|---|---|---|---|---|
| 3 | CATGCCATGGCTAAA AAATTACTCTTTACT TC | <210> SEQ ID NO: 15 <211> 32 <212> DNA <213> Lawsonia | 32 bp | CGCGGATCCGAAAGG CCAGAGGGTATCCA | <210> SEQ ID NO: 16 <211> 29 <212> DNA <213> Lawsonia | 29 bp |
| 5 | CATGCCATGGCTTCG ATCAATACACTTTTC GG | <210> SEQ ID NO: 17 <211> 32 <212> DNA <213> Lawsonia | 32 bp | CGCGGATCCCTGTTT TAAAGAAAGTAAAG | <210> SEQ ID NO: 18 <211> 29 <212> DNA <213> Lawsonia | 29 bp |
| 7 | CATGCCATGGCTAGG GTTACCCACCAATCA AT | <210> SEQ ID NO: 19 <211> 32 <212> DNA <213> Lawsonia | 32 bp | CGCGGATCCAATGTA TTTTGTTAAATTTA | <210> SEQ ID NO: 20 <211> 29 <212> DNA <213> Lawsonia | 29 bp |
| 9 | CATGCCATGGCTATT TCATTAAATAATTCA TC | <210> SEQ ID NO: 21 <211> 32 <212> DNA <213> Lawsonia | 32 bp | CGCGGATCCCGCCAG AATACGCTGTGTTG | <210> SEQ ID NO: 22 <211> 29 <212> DNA <213> Lawsonia | 29 bp |
| 1 | CATGCCATGGCTTCT TTGGTCATTAACAAC AA | <210> SEQ ID NO: 23 <211> 32 <212> DNA <213> Lawsonia | 32 bp | CGCGGATCCGCCACT AATGAGTTGGCTTG | <210> SEQ ID NO: 24 <211> 29 <212> DNA <213> Lawsonia | 29 bp |

TABLE 2

Overview of plasmids comprising the cloned *Lawsonia intracellularis* genes.

| gene | T7 expression vector | cloning sites | calculated molecular mass | plasmid |
|---|---|---|---|---|
| seq id 11 | pET22b | NcoI BamHI | 30.7 kDa | pET 31.4 |
| seq id 3 | pETHIS1 | NcoI BamHI | 26.4 kDa | pET 24.8 |
| seq id 5 | pETHIS1 | NcoI BamHI | 78.3 kDa | pET 76.7 |
| seq id 7 | pETHIS1 | NcoI BamHI | 58.4 kDa | pET 56.8 |
| seq id 9 | pETHIS1 | NcoI BamHI | 28.8 kDa | pET 28.8 |
| seq d 1 | pETHIS1 | NcoI BamHI | 32.6 kDa | pET 31.0 |

Results

Cloning of *Lawsonia* Genes in T7 Based Expression Vectors

*Lawsonia* genes were amplified by PCR using primers listed in table 1. The obtained PCR products were digested using restriction enzymes NcoI and BamHI. The digested PCR products were subsequently ligated to pET22b or pET-HIS1 that had been cut with the same two restriction enzymes as indicated in table 2. The ligation mixtures were transformed to *E. coli* TOP10F and incubated o/n at 37° C. Putative transformants were checked for the right plasmid using colony PCR. This resulted in 6 different expression plasmids. These plasmids were checked by nucleotide sequence analysis and sequences were as expected on basis of the cloning strategy.

Expression of *Lawsonia* Genes from T7 Promoter in *Escherichia coli*

All plasmids listed in table 2 were tested for recombinant protein production. Plasmids were transformed to BL21star (DE3)pLysSrare and an induction was performed. The induction cultures were analysed by SDS-PAGE gel electrophoresis and CBB staining (FIG. 1). All six genes gave sufficient expression in *E. coli* BL21star(DE3) pLysSrare. Expression levels of 150 µg/ml were reached.

Analysis of Expression Products by Western Blot

Figure 2:
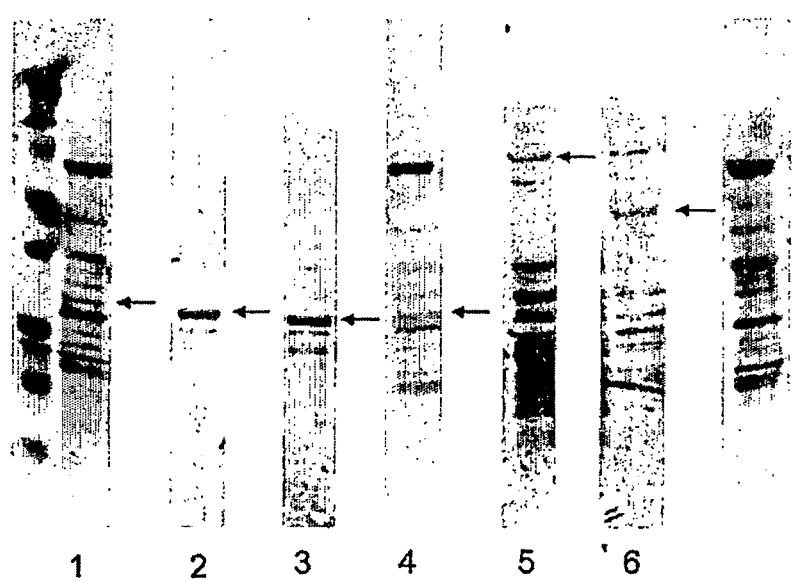

Expression products were analysed by western blot using serum of chickens vaccinated with whole *Lawsonia* cells and serum from a pig that displayed clinical signs and post mortem lesions that are typical for *L. intracellularis* (FIG. 2). The recombinant *Lawsonia* proteins were positively identified by the chicken and pig sera.

LEGENDS TO THE FIGURES

FIG. 1. Analysis of the over-expression of *Lawsonia intracellularis* genes in *Escherichia coli* BL21STAR/pLysS-RARE by NUPAGE.

Lane 1, molecular weight marker; lane 2, pET76.7 T=0; lane 3, pET76.7 T=3; lane 4, pET56.8 T=0; lane 5, pET56.8 T=3; lane 6, pET24.8 T=0; lane 7, pET24.8 T=3; lane 8, pET28.8 T=0; lane 9, pET28.8 T=3; lane 10, pET31.0 T=0; lane 11, pET31.0 T=3; lane 12, pET31.4 T=0; lane 13, pET31.4 T=3; lane 14, T=3 no expression vector.

Arrows indicate the location of the expression products.

FIG. 2. Western blotting of expression products of *Lawsonia intracellularis* genes in *Escherichia coli* BL21STAR/pLysSRARE.

Lane 1, pET31.4; lane 2, pET28.8; lane 3, pET31.0; lane 4, pET24.8; lane 5, pET 76.7; lane 6, pET56.8; lane 7, no expression vector.

Arrows indicate the location of the expression products.

The invention claimed is:

1. An isolated and purified *Lawsonia intracellularis* protein, comprising the amino acid sequence of SEQ ID NO: 2.

2. A composition comprising the protein of claim 1 and a pharmaceutically acceptable carrier.

3. A diagnostic test for the detection of antibodies against *Lawsonia intracellularis*, comprising the protein as defined in claim 1.

* * * * *

UNITED STATES PATENT AND TRADEMARK OFFICE
CERTIFICATE OF CORRECTION

PATENT NO.       : 7,662,390 B2
APPLICATION NO. : 10/571490
DATED            : February 16, 2010
INVENTOR(S)      : Paul Vermeij It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 321 days.

Signed and Sealed this

Thirtieth Day of November, 2010

David J. Kappos
*Director of the United States Patent and Trademark Office*

SEQUENCE LISTING

<160> NUMBER OF SEQ ID NOS: 24

<210> SEQ ID NO 1
<211> LENGTH: 1004
<212> TYPE: DNA
<213> ORGANISM: Lawsonia intracellularis
<220> FEATURE:
<221> NAME/KEY: CDS
<222> LOCATION: (55)..(939)

<400> SEQUENCE: 1

```
tggtatatcc attgcatgat ttatggtaac caaccatttc aggaggtttg ccat atg          57
                                                              Met
                                                              1 tct ttg gtc att aac aac aac atg atg gct gca aat gca gcc cgt aac         105
Ser Leu Val Ile Asn Asn Asn Met Met Ala Ala Asn Ala Ala Arg Asn
          5                  10                  15 ctc aat gaa agt tat tca cga ctt agc caa tca aca aga cgt cta tct         153
Leu Asn Glu Ser Tyr Ser Arg Leu Ser Gln Ser Thr Arg Arg Leu Ser
             20                  25                  30 tct gga ctt cgt gtt ggg aca gca gct gat gat tca gcg ggg ctt gct         201
Ser Gly Leu Arg Val Gly Thr Ala Ala Asp Asp Ser Ala Gly Leu Ala
 35                  40                  45 att aga gaa ctt atg cga gcc gat att aaa aca ttt caa caa ggt gca         249
Ile Arg Glu Leu Met Arg Ala Asp Ile Lys Thr Phe Gln Gln Gly Ala
 50                  55                  60                  65 aga aat gca aat gat gct att tca tta gta caa gtt gca gat ggg gca         297
Arg Asn Ala Asn Asp Ala Ile Ser Leu Val Gln Val Ala Asp Gly Ala
                 70                  75                  80 cta ggt gtt ata gat gaa aag ctt atc cga atg aaa gag ctt gct gaa         345
Leu Gly Val Ile Asp Glu Lys Leu Ile Arg Met Lys Glu Leu Ala Glu
             85                  90                  95 caa gct gct aca ggt act tat aat tca aca caa cgc ttg att att gaa         393
Gln Ala Ala Thr Gly Thr Tyr Asn Ser Thr Gln Arg Leu Ile Ile Glu
        100                 105                 110 tct gaa tat caa gca atg gct tca gaa att aca cgt att tct gtt gca         441
Ser Glu Tyr Gln Ala Met Ala Ser Glu Ile Thr Arg Ile Ser Val Ala
    115                 120                 125 aca gaa ttt aat ggt ata aaa tta tta gat ggt tct cta tct gga cct         489
Thr Glu Phe Asn Gly Ile Lys Leu Leu Asp Gly Ser Leu Ser Gly Pro
130                 135                 140                 145 cat aaa gga act aat cta caa caa aca gga gct cta aga gta cat ttt         537
His Lys Gly Thr Asn Leu Gln Gln Thr Gly Ala Leu Arg Val His Phe
                150                 155                 160 ggt cca ggg aat agt tca gca gaa gac tat tat gaa att agc ata cat         585
Gly Pro Gly Asn Ser Ser Ala Glu Asp Tyr Tyr Glu Ile Ser Ile His
            165                 170                 175 tcc gct aca gct tct gca cta ggc ctt gga aat gga act act ggt cct         633
Ser Ala Thr Ala Ser Ala Leu Gly Leu Gly Asn Gly Thr Thr Gly Pro
        180                 185                 190 ggt gct aca atc tct act caa gct gca gca caa gca gcg tta gac gcc         681
Gly Ala Thr Ile Ser Thr Gln Ala Ala Ala Gln Ala Ala Leu Asp Ala
    195                 200                 205 atc aat gat gct atc gtt tct aaa gat aat att cgt gct agc ctt ggt         729
Ile Asn Asp Ala Ile Val Ser Lys Asp Asn Ile Arg Ala Ser Leu Gly
210                 215                 220                 225 acg cta caa aat agg tta gaa gca aca att aca aac tta aat acc caa         777
Thr Leu Gln Asn Arg Leu Glu Ala Thr Ile Thr Asn Leu Asn Thr Gln
                230                 235                 240
```

```
gct gaa aac ctc cag gct gca gaa tca cga att tct gat ata gac gtt        825
Ala Glu Asn Leu Gln Ala Ala Glu Ser Arg Ile Ser Asp Ile Asp Val
        245                 250                 255 tca aca gaa atg act gaa ttt gta aga aat caa att tta aca caa tct        873
Ser Thr Glu Met Thr Glu Phe Val Arg Asn Gln Ile Leu Thr Gln Ser
    260                 265                 270 gga gta gca atg ctt tca cag gca aac tca ctg cca aag atg gca agc        921
Gly Val Ala Met Leu Ser Gln Ala Asn Ser Leu Pro Lys Met Ala Ser
275                 280                 285 caa ctc att agt ggc taa tccatcacta cataatatgg ttaaggcaga              969
Gln Leu Ile Ser Gly
290 ccaaagacac atggcttgga ggaaagaagt tgttg                                1004
```

<210> SEQ ID NO 2
<211> LENGTH: 294
<212> TYPE: PRT
<213> ORGANISM: Lawsonia intracellularis

<400> SEQUENCE: 2

```
Met Ser Leu Val Ile Asn Asn Met Met Ala Ala Asn Ala Ala Arg
1               5                   10                  15

Asn Leu Asn Glu Ser Tyr Ser Arg Leu Ser Gln Ser Thr Arg Arg Leu
                20                  25                  30

Ser Ser Gly Leu Arg Val Gly Thr Ala Ala Asp Asp Ser Ala Gly Leu
            35                  40                  45

Ala Ile Arg Glu Leu Met Arg Ala Asp Ile Lys Thr Phe Gln Gln Gly
        50                  55                  60

Ala Arg Asn Ala Asn Asp Ala Ile Ser Leu Val Gln Val Ala Asp Gly
65                  70                  75                  80

Ala Leu Gly Val Ile Asp Glu Lys Leu Ile Arg Met Lys Glu Leu Ala
                85                  90                  95

Glu Gln Ala Ala Thr Gly Thr Tyr Asn Ser Thr Gln Arg Leu Ile Ile
            100                 105                 110

Glu Ser Glu Tyr Gln Ala Met Ala Ser Glu Ile Thr Arg Ile Ser Val
        115                 120                 125

Ala Thr Glu Phe Asn Gly Ile Lys Leu Leu Asp Gly Ser Leu Ser Gly
    130                 135                 140

Pro His Lys Gly Thr Asn Leu Gln Gln Thr Gly Ala Leu Arg Val His
145                 150                 155                 160

Phe Gly Pro Gly Asn Ser Ser Ala Glu Asp Tyr Tyr Glu Ile Ser Ile
                165                 170                 175

His Ser Ala Thr Ala Ser Ala Leu Gly Leu Gly Asn Gly Thr Thr Gly
            180                 185                 190

Pro Gly Ala Thr Ile Ser Thr Gln Ala Ala Ala Gln Ala Ala Leu Asp
        195                 200                 205

Ala Ile Asn Asp Ala Ile Val Ser Lys Asp Asn Ile Arg Ala Ser Leu
    210                 215                 220

Gly Thr Leu Gln Asn Arg Leu Glu Ala Thr Ile Thr Asn Leu Asn Thr
225                 230                 235                 240

Gln Ala Glu Asn Leu Gln Ala Ala Glu Ser Arg Ile Ser Asp Ile Asp
                245                 250                 255

Val Ser Thr Glu Met Thr Glu Phe Val Arg Asn Gln Ile Leu Thr Gln
            260                 265                 270

Ser Gly Val Ala Met Leu Ser Gln Ala Asn Ser Leu Pro Lys Met Ala
        275                 280                 285
```

Ser Gln Leu Ile Ser Gly
    290

<210> SEQ ID NO 3
<211> LENGTH: 764
<212> TYPE: DNA
<213> ORGANISM: Lawsonia intracellularis
<220> FEATURE:
<221> NAME/KEY: CDS
<222> LOCATION: (25)..(717)

<400> SEQUENCE: 3

```
acgctaacgt attggaaacc catt atg aaa aaa tta ctc ttt act tca ggc          51
                         Met Lys Lys Leu Leu Phe Thr Ser Gly
                           1               5 tgt att ctt att tta aca ggt tgt tct gct cca aac aaa act cct gtt         99
Cys Ile Leu Ile Leu Thr Gly Cys Ser Ala Pro Asn Lys Thr Pro Val
 10              15                  20                  25 gtt gct cct cct ata aca cct cct cca gca tat gta gaa cct gaa gac        147
Val Ala Pro Pro Ile Thr Pro Pro Pro Ala Tyr Val Glu Pro Glu Asp
                 30                  35                  40 tcc tat agt aat cct ggc tct ctt tac tca tct gct gaa tct gat ggt        195
Ser Tyr Ser Asn Pro Gly Ser Leu Tyr Ser Ser Ala Glu Ser Asp Gly
             45                  50                  55 ctt ttt gct gat act cgt gct cga cgt gta ggt gat att gtt atg gta        243
Leu Phe Ala Asp Thr Arg Ala Arg Arg Val Gly Asp Ile Val Met Val
         60                  65                  70 aaa att gta gaa aat aat act gct aaa aat aaa gca gat aca aca gct        291
Lys Ile Val Glu Asn Asn Thr Ala Lys Asn Lys Ala Asp Thr Thr Ala
 75                  80                  85 gat aaa aaa act gca aat aca tac gga att gat gcg ttt ttt ggt aga        339
Asp Lys Lys Thr Ala Asn Thr Tyr Gly Ile Asp Ala Phe Phe Gly Arg
 90                  95                 100                 105 caa tat att ggt gga gga tca aca aaa att cct gta ggt agt gtt gct        387
Gln Tyr Ile Gly Gly Gly Ser Thr Lys Ile Pro Val Gly Ser Val Ala
             110                 115                 120 ttt gat aca acc tct gaa agt gga acc act agt aca gga gaa aca aaa        435
Phe Asp Thr Thr Ser Glu Ser Gly Thr Thr Ser Thr Gly Glu Thr Lys
         125                 130                 135 cgt gaa gga gct ata aat gga aca att gct gct cgt gta tta cga gtt        483
Arg Glu Gly Ala Ile Asn Gly Thr Ile Ala Ala Arg Val Leu Arg Val
     140                 145                 150 atg cca ggt gga tta tta gaa ata gaa ggc gtc cgt gaa aca cgt gta        531
Met Pro Gly Gly Leu Leu Glu Ile Glu Gly Val Arg Glu Thr Arg Val
 155                 160                 165 aat aat gaa aca cag tat att gtt atc aca gga ctt ata cga cca atg        579
Asn Asn Glu Thr Gln Tyr Ile Val Ile Thr Gly Leu Ile Arg Pro Met
170                 175                 180                 185 gat ata gag cca gac aac tcc att atg tca aat aga atc tct gat gca        627
Asp Ile Glu Pro Asp Asn Ser Ile Met Ser Asn Arg Ile Ser Asp Ala
             190                 195                 200 aaa att gct tat tat ggt caa ggt gtt ctt tcc gag aaa caa aaa cct        675
Lys Ile Ala Tyr Tyr Gly Gln Gly Val Leu Ser Glu Lys Gln Lys Pro
         205                 210                 215 ggt tgg ttt aca cgc ttt atg gat acc ctc tgg cct ttc tag              717
Gly Trp Phe Thr Arg Phe Met Asp Thr Leu Trp Pro Phe
     220                 225                 230 tagtctaata tactaagtat aactcaatat ctataaggta aacgtat                    764
```

<210> SEQ ID NO 4

```
<211> LENGTH: 230
<212> TYPE: PRT
<213> ORGANISM: Lawsonia intracellularis

<400> SEQUENCE: 4

Met Lys Lys Leu Leu Phe Thr Ser Gly Cys Ile Leu Ile Leu Thr Gly
1               5                   10                  15

Cys Ser Ala Pro Asn Lys Thr Pro Val Val Ala Pro Pro Ile Thr Pro
            20                  25                  30

Pro Pro Ala Tyr Val Glu Pro Glu Asp Ser Tyr Ser Asn Pro Gly Ser
        35                  40                  45

Leu Tyr Ser Ser Ala Glu Ser Asp Gly Leu Phe Ala Asp Thr Arg Ala
50                  55                  60

Arg Arg Val Gly Asp Ile Val Met Val Lys Ile Val Glu Asn Asn Thr
65                  70                  75                  80

Ala Lys Asn Lys Ala Asp Thr Thr Ala Asp Lys Lys Thr Ala Asn Thr
                85                  90                  95

Tyr Gly Ile Asp Ala Phe Phe Gly Arg Gln Tyr Ile Gly Gly Gly Ser
            100                 105                 110

Thr Lys Ile Pro Val Gly Ser Val Ala Phe Asp Thr Thr Ser Glu Ser
        115                 120                 125

Gly Thr Thr Ser Thr Gly Glu Thr Lys Arg Glu Gly Ala Ile Asn Gly
130                 135                 140

Thr Ile Ala Ala Arg Val Leu Arg Val Met Pro Gly Gly Leu Leu Glu
145                 150                 155                 160

Ile Glu Gly Val Arg Glu Thr Arg Val Asn Asn Glu Thr Gln Tyr Ile
                165                 170                 175

Val Ile Thr Gly Leu Ile Arg Pro Met Asp Ile Glu Pro Asp Asn Ser
            180                 185                 190

Ile Met Ser Asn Arg Ile Ser Asp Ala Lys Ile Ala Tyr Tyr Gly Gln
        195                 200                 205

Gly Val Leu Ser Glu Lys Gln Lys Pro Gly Trp Phe Thr Arg Phe Met
210                 215                 220

Asp Thr Leu Trp Pro Phe
225                 230

<210> SEQ ID NO 5
<211> LENGTH: 2200
<212> TYPE: DNA
<213> ORGANISM: Lawsonia intracellularis
<220> FEATURE:
<221> NAME/KEY: CDS
<222> LOCATION: (47)..(2164)

<400> SEQUENCE: 5
atcaccattc acgtcctgag ggcacccttc tttctgggag attgta atg tcg atc         55
                                              Met Ser Ile
                                                1 aat aca ctt ttc ggt att ggg aaa agt gca ata gct gga aac cag aca       103
Asn Thr Leu Phe Gly Ile Gly Lys Ser Ala Ile Ala Gly Asn Gln Thr
    5                   10                  15 gct cta aac gtt act ggt aat aat ata gca aat gtt aat aca caa gga       151
Ala Leu Asn Val Thr Gly Asn Asn Ile Ala Asn Val Asn Thr Gln Gly
20                  25                  30                  35 tat tcc cgc caa agt gta cgc ttc gaa gat agg tat gga ctt aat caa       199
Tyr Ser Arg Gln Ser Val Arg Phe Glu Asp Arg Tyr Gly Leu Asn Gln
                40                  45                  50 act cca gga atg ctt ggg cag ggt gtc cat aca gct gaa ata tac cgc       247
```

```
                Thr Pro Gly Met Leu Gly Gln Gly Val His Thr Ala Glu Ile Tyr Arg
                            55                  60                  65 aat ttt aat aga ttt gta gaa gat gct tac ctt aat cgt ttt tcc caa              295
Asn Phe Asn Arg Phe Val Glu Asp Ala Tyr Leu Asn Arg Phe Ser Gln
            70                  75                  80 aat act cga tgg gac gaa caa agt gct att atg aac tct ata gaa agc              343
Asn Thr Arg Trp Asp Glu Gln Ser Ala Ile Met Asn Ser Ile Glu Ser
        85                  90                  95 att ttt aac gaa tca aac cgt aca gga att agt tca cta cta gga gaa              391
Ile Phe Asn Glu Ser Asn Arg Thr Gly Ile Ser Ser Leu Leu Gly Glu
100                 105                 110                 115 ttt ttt aaa gga tgg caa aat ctt tcc tta cgt cca gaa gat gca gct              439
Phe Phe Lys Gly Trp Gln Asn Leu Ser Leu Arg Pro Glu Asp Ala Ala
                120                 125                 130 act cgt gaa gca gtg ctc tct aca gct aaa aat ctc aca caa ctt att              487
Thr Arg Glu Ala Val Leu Ser Thr Ala Lys Asn Leu Thr Gln Leu Ile
            135                 140                 145 aac gat gca aaa tca agt cta caa aaa acc caa caa gaa atg gat ctc              535
Asn Asp Ala Lys Ser Ser Leu Gln Lys Thr Gln Gln Glu Met Asp Leu
        150                 155                 160 tac atc caa caa agt gtt aat aaa gtt aat gag tta gta gat gct att              583
Tyr Ile Gln Gln Ser Val Asn Lys Val Asn Glu Leu Val Asp Ala Ile
165                 170                 175 aaa aac att aat aaa caa atc tca gca act tat att cct ggt caa caa              631
Lys Asn Ile Asn Lys Gln Ile Ser Ala Thr Tyr Ile Pro Gly Gln Gln
180                 185                 190                 195 aac cct aat caa tta ctt gat caa cga gat caa ctt gtt cga gaa tta              679
Asn Pro Asn Gln Leu Leu Asp Gln Arg Asp Gln Leu Val Arg Glu Leu
                200                 205                 210 gca aac ctg gta gat ata gaa gta aag gat aaa ggt gga gga aat ttt              727
Ala Asn Leu Val Asp Ile Glu Val Lys Asp Lys Gly Gly Gly Asn Phe
            215                 220                 225 gat ata caa tta aaa tct gga caa cct ctc ctg gaa gga caa ata ggt              775
Asp Ile Gln Leu Lys Ser Gly Gln Pro Leu Leu Glu Gly Gln Ile Gly
        230                 235                 240 tat aca ctt agc gtt ggg gga caa cga gtt gaa aac tat tta aaa caa              823
Tyr Thr Leu Ser Val Gly Gly Gln Arg Val Glu Asn Tyr Leu Lys Gln
245                 250                 255 gat tca aaa tat aca ggc act ata acc tct agt ggt tca gac tcc cat              871
Asp Ser Lys Tyr Thr Gly Thr Ile Thr Ser Ser Gly Ser Asp Ser His
260                 265                 270                 275 gaa tat tca ttt gaa att att aat cct cct tct ggt gga gca cct ggg              919
Glu Tyr Ser Phe Glu Ile Ile Asn Pro Pro Ser Gly Gly Ala Pro Gly
                280                 285                 290 agt atg cgt gta tca ctt gat gga gga aaa act tgg ctt cgt aac gaa              967
Ser Met Arg Val Ser Leu Asp Gly Gly Lys Thr Trp Leu Arg Asn Glu
            295                 300                 305 gat gga tct gaa ctt aac gta cct att cct act acg cct ggt gaa act             1015
Asp Gly Ser Glu Leu Asn Val Pro Ile Pro Thr Thr Pro Gly Glu Thr
        310                 315                 320 atc aaa gta aaa aat ctt gaa ata tct ttt gat caa gat cct tcg caa             1063
Ile Lys Val Lys Asn Leu Glu Ile Ser Phe Asp Gln Asp Pro Ser Gln
325                 330                 335 tta gtt tca gga gac agg ttt gat gtt att cca aaa aca ggt tta tac             1111
Leu Val Ser Gly Asp Arg Phe Asp Val Ile Pro Lys Thr Gly Leu Tyr
340                 345                 350                 355 tgg aat tca ccc aca aga cct ccg atc aat att act ccc caa aca cta             1159
Trp Asn Ser Pro Thr Arg Pro Pro Ile Asn Ile Thr Pro Gln Thr Leu
                360                 365                 370
```

```
                                                -continued aat gat ggt aca gaa aat aca ggg cgt ctc act gga gga aaa ctt act   1207
Asn Asp Gly Thr Glu Asn Thr Gly Arg Leu Thr Gly Gly Lys Leu Thr
            375                 380                 385 gca tat ttt agt act cgt gat tat aat gca gga aga tat att gat aaa   1255
Ala Tyr Phe Ser Thr Arg Asp Tyr Asn Ala Gly Arg Tyr Ile Asp Lys
        390                 395                 400 ctt gat gca tta gca aac tct att gta tgg gaa gta aac cga atc cac   1303
Leu Asp Ala Leu Ala Asn Ser Ile Val Trp Glu Val Asn Arg Ile His
    405                 410                 415 agt caa ggt gct gga gaa caa aaa atg act tac tct tta ggg agt agt   1351
Ser Gln Gly Ala Gly Glu Gln Lys Met Thr Tyr Ser Leu Gly Ser Ser
420                 425                 430                 435 caa gta aat cgt aca gat gta cca ctg gga aca tct caa tct ggt ctt   1399
Gln Val Asn Arg Thr Asp Val Pro Leu Gly Thr Ser Gln Ser Gly Leu
                440                 445                 450 gcc tat gga aac cgt ctt aca act ggg aac tta tca ttc caa atc tat   1447
Ala Tyr Gly Asn Arg Leu Thr Thr Gly Asn Leu Ser Phe Gln Ile Tyr
            455                 460                 465 gat gaa aat gga aaa cct tta cct gta ggc aca cct cca aat gga atc   1495
Asp Glu Asn Gly Lys Pro Leu Pro Val Gly Thr Pro Pro Asn Gly Ile
        470                 475                 480 cca gaa tct tta gat ctt gat cca ggt acg cct gga gtt caa aac ttt   1543
Pro Glu Ser Leu Asp Leu Asp Pro Gly Thr Pro Gly Val Gln Asn Phe
    485                 490                 495 gat cct tca att cat agt ctt gaa gat cta gtt aat gcc att aac cac   1591
Asp Pro Ser Ile His Ser Leu Glu Asp Leu Val Asn Ala Ile Asn His
500                 505                 510                 515 cct aat aac tat ggt gaa ttt atg aaa gct tct att gtt aat gga agt   1639
Pro Asn Asn Tyr Gly Glu Phe Met Lys Ala Ser Ile Val Asn Gly Ser
                520                 525                 530 ctc caa ctt acc agt cgt cct gga aca tca ttt gca gca aaa aca gat   1687
Leu Gln Leu Thr Ser Arg Pro Gly Thr Ser Phe Ala Ala Lys Thr Asp
            535                 540                 545 aca aca ggt tta ctt gca gcc ctt gga atc aat act ttt ttc caa ggt   1735
Thr Thr Gly Leu Leu Ala Ala Leu Gly Ile Asn Thr Phe Phe Gln Gly
        550                 555                 560 tca gat gct aca gat atg gct ata aaa cct gat gtt att caa aat aca   1783
Ser Asp Ala Thr Asp Met Ala Ile Lys Pro Asp Val Ile Gln Asn Thr
    565                 570                 575 aat ttt att aat gct gga aag gtt aat gct aat ggt gaa gtt tct aca   1831
Asn Phe Ile Asn Ala Gly Lys Val Asn Ala Asn Gly Glu Val Ser Thr
580                 585                 590                 595 ggt gat aat agt ata gct aaa gaa ctt gct gac ctt gct aca aaa gaa   1879
Gly Asp Asn Ser Ile Ala Lys Glu Leu Ala Asp Leu Ala Thr Lys Glu
                600                 605                 610 gta aca att tct act gga tgg gaa act aca cac caa aca tta ggt gct   1927
Val Thr Ile Ser Thr Gly Trp Glu Thr Thr His Gln Thr Leu Gly Ala
            615                 620                 625 tat tat ggt gca cta gtt ggt ctt gta gga tct gat act cgt aca gca   1975
Tyr Tyr Gly Ala Leu Val Gly Leu Val Gly Ser Asp Thr Arg Thr Ala
        630                 635                 640 aaa ttt aat gct gat tat aat aaa aca ctt tca aac gaa cta gaa caa   2023
Lys Phe Asn Ala Asp Tyr Asn Lys Thr Leu Ser Asn Glu Leu Glu Gln
    645                 650                 655 caa gct tta tct att aca ggc gtt aac cta gat gaa gaa atg act cag   2071
Gln Ala Leu Ser Ile Thr Gly Val Asn Leu Asp Glu Glu Met Thr Gln
660                 665                 670                 675 ctt att aaa ttt caa cat tca tat act gca gca gca aaa ctc att aca   2119
Leu Ile Lys Phe Gln His Ser Tyr Thr Ala Ala Ala Lys Leu Ile Thr
                680                 685                 690
```

```
aca gca gat caa atg ctg caa act tta ctt tct tta aaa cag tag        2164
Thr Ala Asp Gln Met Leu Gln Thr Leu Leu Ser Leu Lys Gln
            695                 700                 705 ggagtaaaca tgagggttac ccaccaatca atgtat                            2200
```

<210> SEQ ID NO 6
<211> LENGTH: 705
<212> TYPE: PRT
<213> ORGANISM: Lawsonia intracellularis

<400> SEQUENCE: 6

```
Met Ser Ile Asn Thr Leu Phe Gly Ile Gly Lys Ser Ala Ile Ala Gly
1               5                   10                  15

Asn Gln Thr Ala Leu Asn Val Thr Gly Asn Asn Ile Ala Asn Val Asn
            20                  25                  30

Thr Gln Gly Tyr Ser Arg Gln Ser Val Arg Phe Glu Asp Arg Tyr Gly
        35                  40                  45

Leu Asn Gln Thr Pro Gly Met Leu Gly Gln Gly Val His Thr Ala Glu
    50                  55                  60

Ile Tyr Arg Asn Phe Asn Arg Phe Val Glu Asp Ala Tyr Leu Asn Arg
65                  70                  75                  80

Phe Ser Gln Asn Thr Arg Trp Asp Glu Gln Ser Ala Ile Met Asn Ser
                85                  90                  95

Ile Glu Ser Ile Phe Asn Glu Ser Asn Arg Thr Gly Ile Ser Ser Leu
            100                 105                 110

Leu Gly Glu Phe Phe Lys Gly Trp Gln Asn Leu Ser Leu Arg Pro Glu
        115                 120                 125

Asp Ala Ala Thr Arg Glu Ala Val Leu Ser Thr Ala Lys Asn Leu Thr
    130                 135                 140

Gln Leu Ile Asn Asp Ala Lys Ser Ser Leu Gln Lys Thr Gln Gln Glu
145                 150                 155                 160

Met Asp Leu Tyr Ile Gln Ser Val Asn Lys Val Asn Glu Leu Val
                165                 170                 175

Asp Ala Ile Lys Asn Ile Asn Lys Gln Ile Ser Ala Thr Tyr Ile Pro
            180                 185                 190

Gly Gln Gln Asn Pro Asn Gln Leu Leu Asp Gln Arg Asp Gln Leu Val
        195                 200                 205

Arg Glu Leu Ala Asn Leu Val Asp Ile Glu Val Lys Asp Lys Gly Gly
    210                 215                 220

Gly Asn Phe Asp Ile Gln Leu Lys Ser Gly Gln Pro Leu Leu Glu Gly
225                 230                 235                 240

Gln Ile Gly Tyr Thr Leu Ser Val Gly Gly Gln Arg Val Glu Asn Tyr
                245                 250                 255

Leu Lys Gln Asp Ser Lys Tyr Thr Gly Thr Ile Thr Ser Ser Gly Ser
            260                 265                 270

Asp Ser His Glu Tyr Ser Phe Glu Ile Ile Asn Pro Ser Gly Gly
        275                 280                 285

Ala Pro Gly Ser Met Arg Val Ser Leu Asp Gly Gly Lys Thr Trp Leu
    290                 295                 300

Arg Asn Glu Asp Gly Ser Glu Leu Asn Val Pro Ile Pro Thr Thr Pro
305                 310                 315                 320

Gly Glu Thr Ile Lys Val Lys Asn Leu Glu Ile Ser Phe Asp Gln Asp
                325                 330                 335

Pro Ser Gln Leu Val Ser Gly Asp Arg Phe Asp Val Ile Pro Lys Thr
```

340                 345                 350
Gly Leu Tyr Trp Asn Ser Pro Thr Arg Pro Ile Asn Ile Thr Pro
            355                 360                 365

Gln Thr Leu Asn Asp Gly Thr Glu Asn Thr Gly Arg Leu Thr Gly Gly
    370                 375                 380

Lys Leu Thr Ala Tyr Phe Ser Thr Arg Asp Tyr Asn Ala Gly Arg Tyr
385                 390                 395                 400

Ile Asp Lys Leu Asp Ala Leu Ala Asn Ser Ile Val Trp Glu Val Asn
                405                 410                 415

Arg Ile His Ser Gln Gly Ala Gly Glu Gln Lys Met Thr Tyr Ser Leu
            420                 425                 430

Gly Ser Ser Gln Val Asn Arg Thr Asp Val Pro Leu Gly Thr Ser Gln
        435                 440                 445

Ser Gly Leu Ala Tyr Gly Asn Arg Leu Thr Thr Gly Asn Leu Ser Phe
    450                 455                 460

Gln Ile Tyr Asp Glu Asn Gly Lys Pro Leu Pro Val Gly Thr Pro Pro
465                 470                 475                 480

Asn Gly Ile Pro Glu Ser Leu Asp Leu Asp Pro Gly Thr Pro Gly Val
                485                 490                 495

Gln Asn Phe Asp Pro Ser Ile His Ser Leu Glu Asp Leu Val Asn Ala
            500                 505                 510

Ile Asn His Pro Asn Asn Tyr Gly Glu Phe Met Lys Ala Ser Ile Val
        515                 520                 525

Asn Gly Ser Leu Gln Leu Thr Ser Arg Pro Gly Thr Ser Phe Ala Ala
    530                 535                 540

Lys Thr Asp Thr Thr Gly Leu Leu Ala Ala Leu Gly Ile Asn Thr Phe
545                 550                 555                 560

Phe Gln Gly Ser Asp Ala Thr Asp Met Ala Ile Lys Pro Asp Val Ile
                565                 570                 575

Gln Asn Thr Asn Phe Ile Asn Ala Gly Lys Val Asn Ala Asn Gly Glu
            580                 585                 590

Val Ser Thr Gly Asp Asn Ser Ile Ala Lys Glu Leu Ala Asp Leu Ala
        595                 600                 605

Thr Lys Glu Val Thr Ile Ser Thr Gly Trp Glu Thr Thr His Gln Thr
    610                 615                 620

Leu Gly Ala Tyr Tyr Gly Ala Leu Val Gly Leu Val Gly Ser Asp Thr
625                 630                 635                 640

Arg Thr Ala Lys Phe Asn Ala Asp Tyr Asn Lys Thr Leu Ser Asn Glu
                645                 650                 655

Leu Glu Gln Gln Ala Leu Ser Ile Thr Gly Val Asn Leu Asp Glu Glu
            660                 665                 670

Met Thr Gln Leu Ile Lys Phe Gln His Ser Tyr Thr Ala Ala Ala Lys
        675                 680                 685

Leu Ile Thr Thr Ala Asp Gln Met Leu Gln Thr Leu Leu Ser Leu Lys
    690                 695                 700

Gln
705

<210> SEQ ID NO 7
<211> LENGTH: 1740
<212> TYPE: DNA
<213> ORGANISM: Lawsonia intracellularis
<220> FEATURE:
<221> NAME/KEY: CDS
<222> LOCATION: (54)..(1631)

<400> SEQUENCE: 7

```
cagcagatca aatgctgcaa actttacttt ctttaaaaca gtagggagta aac atg                    56
                                                          Met
                                                          1 agg gtt acc cac caa tca atg tat tct ggc atg atc agt cag atg aac                  104
Arg Val Thr His Gln Ser Met Tyr Ser Gly Met Ile Ser Gln Met Asn
        5                  10                 15 aaa agt tta tct gac tat atg gag act aat ata caa ggc ggt aca atg                  152
Lys Ser Leu Ser Asp Tyr Met Glu Thr Asn Ile Gln Gly Gly Thr Met
     20                  25                 30 aaa aga ata aac cgt cct tct gat gat cct gca ggt aca gct aga atc                  200
Lys Arg Ile Asn Arg Pro Ser Asp Asp Pro Ala Gly Thr Ala Arg Ile
 35                  40                 45 ctc tct tat cgt gga agt att ggt gga ata gaa caa ttt aaa aca aat                  248
Leu Ser Tyr Arg Gly Ser Ile Gly Gly Ile Glu Gln Phe Lys Thr Asn
 50                  55                 60                 65 act gat aca gct atg gga tgg tta tct ctt gca gat gaa aca ctt aat                  296
Thr Asp Thr Ala Met Gly Trp Leu Ser Leu Ala Asp Glu Thr Leu Asn
             70                 75                 80 caa gtt tca aca gtt gtt act aaa att aaa gaa ctt gcc gaa caa gct                  344
Gln Val Ser Thr Val Val Thr Lys Ile Lys Glu Leu Ala Glu Gln Ala
             85                 90                 95 gct aca gat aca tat acc cct gac caa cgt gaa gct att ggt ttc caa                  392
Ala Thr Asp Thr Tyr Thr Pro Asp Gln Arg Glu Ala Ile Gly Phe Gln
            100                105                110 ctc cgc caa ctt atg gga act ctt ata aac ctt tca aat aat caa ttt                  440
Leu Arg Gln Leu Met Gly Thr Leu Ile Asn Leu Ser Asn Asn Gln Phe
115                 120                125 gaa ggc aaa cat att ttt tct ggg caa gat tat aat aaa tca tcc ttt                  488
Glu Gly Lys His Ile Phe Ser Gly Gln Asp Tyr Asn Lys Ser Ser Phe
130                 135                140                145 cta gaa gga ctc aca gtc aca agc gga gat ccc aat gtt aac cct aat                  536
Leu Glu Gly Leu Thr Val Thr Ser Gly Asp Pro Asn Val Asn Pro Asn
                150                155                160 cca cca atg cag gtt act gga aca ctt gaa aaa act gga ctt att cgc                  584
Pro Pro Met Gln Val Thr Gly Thr Leu Glu Lys Thr Gly Leu Ile Arg
                165                170                175 ttt gaa aaa gat gaa aca atc cct cca gca gca gat cta aat tat cag                  632
Phe Glu Lys Asp Glu Thr Ile Pro Pro Ala Ala Asp Leu Asn Tyr Gln
                180                185                190 tgg tca act gat ggt ggt aaa act tgg caa act gca acc atc cct gct                  680
Trp Ser Thr Asp Gly Gly Lys Thr Trp Gln Thr Ala Thr Ile Pro Ala
         195                200                205 ggg gga cga gaa ata act ata ggt ggt gca gtc gta act gtt cct gct                  728
Gly Gly Arg Glu Ile Thr Ile Gly Gly Ala Val Val Thr Val Pro Ala
210                 215                220                225 cca gct aca aca aat gta aca gca ttt gac cca gat aaa cct ctt gga                  776
Pro Ala Thr Thr Asn Val Thr Ala Phe Asp Pro Asp Lys Pro Leu Gly
                230                235                240 gat act aat ggt tcc tta cta tat gta cgt cct aca gct ata tac caa                  824
Asp Thr Asn Gly Ser Leu Leu Tyr Val Arg Pro Thr Ala Ile Tyr Gln
         245                250                255 ggg agt gat aat aac tca aaa cct att gta gac aga tat ggc act gta                  872
Gly Ser Asp Asn Asn Ser Lys Pro Ile Val Asp Arg Tyr Gly Thr Val
         260                265                270 cca atg cct cca ctt aat acc aat aca gta ggg act ttt tct gat aat                  920
Pro Met Pro Pro Leu Asn Thr Asn Thr Val Gly Thr Phe Ser Asp Asn
         275                280                285
```

```
gtc gtt gta aaa ttc cct aat ggt gtt gat tta tca act cct gga tca     968
Val Val Val Lys Phe Pro Asn Gly Val Asp Leu Ser Thr Pro Gly Ser
290             295                 300                 305 ttt gat ttc tct tat agt aca gat gga ggc aaa aca tgg aca gca gga    1016
Phe Asp Phe Ser Tyr Ser Thr Asp Gly Gly Lys Thr Trp Thr Ala Gly
                310                 315                 320 aac tct gaa gtc att gtt tct cct gga cca cca tca act agt act gca    1064
Asn Ser Glu Val Ile Val Ser Pro Gly Pro Pro Ser Thr Ser Thr Ala
            325                 330                 335 aga ctc att ctg cct ggt ggc tat atg gat ata ggt tct gct gat act    1112
Arg Leu Ile Leu Pro Gly Gly Tyr Met Asp Ile Gly Ser Ala Asp Thr
        340                 345                 350 aca agt cca aat aat act att cct cct gat gga caa ctt atc ctt cgc    1160
Thr Ser Pro Asn Asn Thr Ile Pro Pro Asp Gly Gln Leu Ile Leu Arg
    355                 360                 365 ccc caa cga aca gat ctt agt ttt gaa atc atg gaa gga caa aat att    1208
Pro Gln Arg Thr Asp Leu Ser Phe Glu Ile Met Glu Gly Gln Asn Ile
370                 375                 380                 385 act gtc aca aat gta gga aaa gat att ttt ggt gga ata tat tct aca    1256
Thr Val Thr Asn Val Gly Lys Asp Ile Phe Gly Gly Ile Tyr Ser Thr
                390                 395                 400 aat ggc tca tct aat ttg gaa cct atg ttt gga caa aat gat gga cgt    1304
Asn Gly Ser Ser Asn Leu Glu Pro Met Phe Gly Gln Asn Asp Gly Arg
            405                 410                 415 aat tta ttt gaa aca gtt gga aat ctt att gcg tac act gaa aca aat    1352
Asn Leu Phe Glu Thr Val Gly Asn Leu Ile Ala Tyr Thr Glu Thr Asn
        420                 425                 430 aat caa gaa ggc att gca aac gcc ctt aaa gat ctt gaa tta gca caa    1400
Asn Gln Glu Gly Ile Ala Asn Ala Leu Lys Asp Leu Glu Leu Ala Gln
    435                 440                 445 aaa aat atc cta act caa gct gca cgt att gga ggt aaa gaa aac cgt    1448
Lys Asn Ile Leu Thr Gln Ala Ala Arg Ile Gly Gly Lys Glu Asn Arg
450                 455                 460                 465 ctt gaa atc aca aaa gaa gct ctt gat aca aat aaa tat gat caa aca    1496
Leu Glu Ile Thr Lys Glu Ala Leu Asp Thr Asn Lys Tyr Asp Gln Thr
                470                 475                 480 caa cgc tta agt ggt gtt gaa gat gca gac ctt aca gaa cta gta agc    1544
Gln Arg Leu Ser Gly Val Glu Asp Ala Asp Leu Thr Glu Leu Val Ser
            485                 490                 495 cgc tta gca caa caa caa atg gct tat tct act ata tta aaa tct tct    1592
Arg Leu Ala Gln Gln Gln Met Ala Tyr Ser Thr Ile Leu Lys Ser Ser
        500                 505                 510 tct atg att atg cag tta aat tta aca aaa tac att taa tctattacta    1641
Ser Met Ile Met Gln Leu Asn Leu Thr Lys Tyr Ile
    515                 520                 525 aatagcaata gtatgaaaaa attctataat taattatcag atggtttaat gatagtacct  1701
ctatgccttt taataattag taaatggagt tgtccatgc                         1740

<210> SEQ ID NO 8
<211> LENGTH: 525
<212> TYPE: PRT
<213> ORGANISM: Lawsonia intracellularis

<400> SEQUENCE: 8

Met Arg Val Thr His Gln Ser Met Tyr Ser Gly Met Ile Ser Gln Met
1               5                   10                  15

Asn Lys Ser Leu Ser Asp Tyr Met Glu Thr Asn Ile Gln Gly Gly Thr
            20                  25                  30

Met Lys Arg Ile Asn Arg Pro Ser Asp Asp Pro Ala Gly Thr Ala Arg
```

-continued

```
                35                  40                  45
Ile Leu Ser Tyr Arg Gly Ser Ile Gly Ile Glu Gln Phe Lys Thr
 50                  55                  60

Asn Thr Asp Thr Ala Met Gly Trp Leu Ser Leu Ala Asp Glu Thr Leu
 65                  70                  75                  80

Asn Gln Val Ser Thr Val Thr Lys Ile Lys Glu Leu Ala Glu Gln
                 85                  90                  95

Ala Ala Thr Asp Thr Tyr Thr Pro Asp Gln Arg Glu Ala Ile Gly Phe
                100                 105                 110

Gln Leu Arg Gln Leu Met Gly Thr Leu Ile Asn Leu Ser Asn Asn Gln
                115                 120                 125

Phe Glu Gly Lys His Ile Phe Ser Gly Gln Asp Tyr Asn Lys Ser Ser
130                 135                 140

Phe Leu Glu Gly Leu Thr Val Thr Ser Gly Asp Pro Asn Val Asn Pro
145                 150                 155                 160

Asn Pro Pro Met Gln Val Thr Gly Thr Leu Glu Lys Thr Gly Leu Ile
                165                 170                 175

Arg Phe Glu Lys Asp Glu Thr Ile Pro Pro Ala Ala Asp Leu Asn Tyr
                180                 185                 190

Gln Trp Ser Thr Asp Gly Gly Lys Thr Trp Gln Thr Ala Thr Ile Pro
                195                 200                 205

Ala Gly Gly Arg Glu Ile Thr Ile Gly Gly Ala Val Val Thr Val Pro
                210                 215                 220

Ala Pro Ala Thr Thr Asn Val Thr Ala Phe Asp Pro Asp Lys Pro Leu
225                 230                 235                 240

Gly Asp Thr Asn Gly Ser Leu Leu Tyr Val Arg Pro Thr Ala Ile Tyr
                245                 250                 255

Gln Gly Ser Asp Asn Asn Ser Lys Pro Ile Val Asp Arg Tyr Gly Thr
                260                 265                 270

Val Pro Met Pro Pro Leu Asn Thr Asn Thr Val Gly Thr Phe Ser Asp
                275                 280                 285

Asn Val Val Lys Phe Pro Asn Gly Val Asp Leu Ser Thr Pro Gly
290                 295                 300

Ser Phe Asp Phe Ser Tyr Ser Thr Asp Gly Gly Lys Thr Trp Thr Ala
305                 310                 315                 320

Gly Asn Ser Glu Val Ile Val Ser Pro Gly Pro Ser Thr Ser Thr
                325                 330                 335

Ala Arg Leu Ile Leu Pro Gly Gly Tyr Met Asp Ile Gly Ser Ala Asp
                340                 345                 350

Thr Thr Ser Pro Asn Asn Thr Ile Pro Pro Asp Gly Gln Leu Ile Leu
                355                 360                 365

Arg Pro Gln Arg Thr Asp Leu Ser Phe Glu Ile Met Glu Gly Gln Asn
370                 375                 380

Ile Thr Val Thr Asn Val Gly Lys Asp Ile Phe Gly Gly Ile Tyr Ser
385                 390                 395                 400

Thr Asn Gly Ser Ser Asn Leu Glu Pro Met Phe Gly Gln Asn Asp Gly
                405                 410                 415

Arg Asn Leu Phe Glu Thr Val Gly Asn Leu Ile Ala Tyr Thr Glu Thr
                420                 425                 430

Asn Asn Gln Glu Gly Ile Ala Asn Ala Leu Lys Asp Leu Glu Leu Ala
                435                 440                 445

Gln Lys Asn Ile Leu Thr Gln Ala Ala Arg Ile Gly Gly Lys Glu Asn
450                 455                 460
```

-continued

```
Arg Leu Glu Ile Thr Lys Glu Ala Leu Asp Thr Asn Lys Tyr Asp Gln
465                 470                 475                 480

Thr Gln Arg Leu Ser Gly Val Glu Asp Ala Asp Leu Thr Glu Leu Val
            485                 490                 495

Ser Arg Leu Ala Gln Gln Met Ala Tyr Ser Thr Ile Leu Lys Ser
        500                 505                 510

Ser Ser Met Ile Met Gln Leu Asn Leu Thr Lys Tyr Ile
    515                 520                 525

<210> SEQ ID NO 9
<211> LENGTH: 902
<212> TYPE: DNA
<213> ORGANISM: Lawsonia intracellularis
<220> FEATURE:
<221> NAME/KEY: CDS
<222> LOCATION: (63)..(842)

<400> SEQUENCE: 9
ctttagtaaa tacagtgact atactataat atataaatta ataaattttg gagaagacta      60 tc atg att tca tta aat aat tca tca att caa ata cca caa caa aat       107
   Met Ile Ser Leu Asn Asn Ser Ser Ile Gln Ile Pro Gln Gln Asn
   1               5                  10                  15 ata gaa gaa agt acc tca caa gaa gta act tcc tcc tct ggt gga caa     155
Ile Glu Glu Ser Thr Ser Gln Glu Val Thr Ser Ser Ser Gly Gly Gln
                20                  25                  30 cct gct aaa gtt gat ggt gta tca atc caa gcc cct aag gct cct gtt     203
Pro Ala Lys Val Asp Gly Val Ser Ile Gln Ala Pro Lys Ala Pro Val
            35                  40                  45 act tct gca gct agt aac tta gaa gga gta cag caa aga gaa gct caa     251
Thr Ser Ala Ala Ser Asn Leu Glu Gly Val Gln Gln Arg Glu Ala Gln
        50                  55                  60 gaa aat gtt aca aaa atg ggc tta cct gag cta tca gct cct aaa ggt     299
Glu Asn Val Thr Lys Met Gly Leu Pro Glu Leu Ser Ala Pro Lys Gly
65                  70                  75 ggt ggt tat gtt cag tca aca gca gct atg ttt gca gaa gtt aca gtt     347
Gly Gly Tyr Val Gln Ser Thr Ala Ala Met Phe Ala Glu Val Thr Val
80                  85                  90                  95 gat gct atg aat cag caa cgt aaa gct gcg caa gac gta caa aat agt     395
Asp Ala Met Asn Gln Gln Arg Lys Ala Ala Gln Asp Val Gln Asn Ser
                100                 105                 110 gct ctt gaa gga atg gtt aat aag atg ctg gaa gca gct aaa gat ata     443
Ala Leu Glu Gly Met Val Asn Lys Met Leu Glu Ala Ala Lys Asp Ile
            115                 120                 125 aaa gaa caa tct aaa tta atg atg ggg tta ggt ata gca agt tct gtt     491
Lys Glu Gln Ser Lys Leu Met Met Gly Leu Gly Ile Ala Ser Ser Val
        130                 135                 140 atg acc act gca atg gga ttt ggg ggt act ata ggt ggt gta aaa agt     539
Met Thr Thr Ala Met Gly Phe Gly Gly Thr Ile Gly Gly Val Lys Ser
145                 150                 155 atg aca gct aac cct gga gta gga aca aca cct caa gca caa gtt act     587
Met Thr Ala Asn Pro Gly Val Gly Thr Thr Pro Gln Ala Gln Val Thr
160                 165                 170                 175 tca aac aag ctt act tta ggt aag gag att gct gaa ggt ata aga ggt     635
Ser Asn Lys Leu Thr Leu Gly Lys Glu Ile Ala Glu Gly Ile Arg Gly
                180                 185                 190 ggt atg gat act ggt aaa gag agt caa gtg aaa tct ata gat gct gat     683
Gly Met Asp Thr Gly Lys Glu Ser Gln Val Lys Ser Ile Asp Ala Asp
            195                 200                 205 ata aga aca act caa gca gaa gaa aag aaa cta gaa gca caa atg gaa     731
```

-continued

```
Ile Arg Thr Thr Gln Ala Glu Glu Lys Lys Leu Glu Ala Gln Met Glu
        210                 215                 220 cta gta aag caa ttt gct gaa aat tca aag aac ctt gct cag caa gct       779
Leu Val Lys Gln Phe Ala Glu Asn Ser Lys Asn Leu Ala Gln Gln Ala
        225                 230                 235 ctg cag att atg tca gaa gtt act agg gat gct aat gca aca aca cag       827
Leu Gln Ile Met Ser Glu Val Thr Arg Asp Ala Asn Ala Thr Thr Gln
240                 245                 250                 255 cgt att ctg gcg taa taatttatag aacaactaat atgaagttat tgagaaataa       882
Arg Ile Leu Ala atatagattg taatatatag                                                 902
```

<210> SEQ ID NO 10
<211> LENGTH: 259
<212> TYPE: PRT
<213> ORGANISM: Lawsonia intracellularis

<400> SEQUENCE: 10

```
Met Ile Ser Leu Asn Asn Ser Ser Ile Gln Ile Pro Gln Gln Asn Ile
1               5                   10                  15

Glu Glu Ser Thr Ser Gln Glu Val Thr Ser Ser Gly Gly Gln Pro
            20                  25                  30

Ala Lys Val Asp Gly Val Ser Ile Gln Ala Pro Lys Ala Pro Val Thr
        35                  40                  45

Ser Ala Ala Ser Asn Leu Glu Gly Val Gln Gln Arg Glu Ala Gln Glu
    50                  55                  60

Asn Val Thr Lys Met Gly Leu Pro Glu Leu Ser Ala Pro Lys Gly Gly
65                  70                  75                  80

Gly Tyr Val Gln Ser Thr Ala Ala Met Phe Ala Glu Val Thr Val Asp
                85                  90                  95

Ala Met Asn Gln Gln Arg Lys Ala Ala Gln Asp Val Gln Asn Ser Ala
            100                 105                 110

Leu Glu Gly Met Val Asn Lys Met Leu Glu Ala Ala Lys Asp Ile Lys
        115                 120                 125

Glu Gln Ser Lys Leu Met Met Gly Leu Gly Ile Ala Ser Ser Val Met
    130                 135                 140

Thr Thr Ala Met Gly Phe Gly Gly Thr Ile Gly Gly Val Lys Ser Met
145                 150                 155                 160

Thr Ala Asn Pro Gly Val Gly Thr Thr Pro Gln Ala Gln Val Thr Ser
                165                 170                 175

Asn Lys Leu Thr Leu Gly Lys Glu Ile Ala Glu Gly Ile Arg Gly Gly
            180                 185                 190

Met Asp Thr Gly Lys Glu Ser Gln Val Lys Ser Ile Asp Ala Asp Ile
        195                 200                 205

Arg Thr Thr Gln Ala Glu Glu Lys Lys Leu Glu Ala Gln Met Glu Leu
    210                 215                 220

Val Lys Gln Phe Ala Glu Asn Ser Lys Asn Leu Ala Gln Gln Ala Leu
225                 230                 235                 240

Gln Ile Met Ser Glu Val Thr Arg Asp Ala Asn Ala Thr Thr Gln Arg
                245                 250                 255

Ile Leu Ala
```

<210> SEQ ID NO 11
<211> LENGTH: 951
<212> TYPE: DNA
<213> ORGANISM: Lawsonia intracellularis

```
<220> FEATURE:
<221> NAME/KEY: CDS
<222> LOCATION: (50)..(877)

<400> SEQUENCE: 11
tgcattaact ttctaaattt ttatttagaa aaacacagag gtaaagata atg ctc ttt      58
                                                      Met Leu Phe
                                                      1 tct ttt cgt ttt att acc tat ccc ctc ata aca att ttt ata tta tat     106
Ser Phe Arg Phe Ile Thr Tyr Pro Leu Ile Thr Ile Phe Ile Leu Tyr
  5                  10                  15 act tgt cat aat gcg ctt gct agt aat aat gat tca atg att acc tct     154
Thr Cys His Asn Ala Leu Ala Ser Asn Asn Asp Ser Met Ile Thr Ser
 20                  25                  30                  35 gaa aat ttt gaa agc caa tta cga ctt ctt ctt cat aac cat cct gag     202
Glu Asn Phe Glu Ser Gln Leu Arg Leu Leu Leu His Asn His Pro Glu
                 40                  45                  50 ctt gtc ctt gat gta cta aga gag cat agc gaa ctt gtc ctt gaa att     250
Leu Val Leu Asp Val Leu Arg Glu His Ser Glu Leu Val Leu Glu Ile
             55                  60                  65 gcc caa caa ggt tct aaa cag cgt caa cat aaa tcc ctt ata gca cag     298
Ala Gln Gln Gly Ser Lys Gln Arg Gln His Lys Ser Leu Ile Ala Gln
         70                  75                  80 tgg aaa aaa gac ata act act cca aaa aat atg cat ctg gaa aat aga     346
Trp Lys Lys Asp Ile Thr Thr Pro Lys Asn Met His Leu Glu Asn Arg
 85                  90                  95 cca atc cga ggg aat cca aaa gca ccc gta act att gta gca ttt tca     394
Pro Ile Arg Gly Asn Pro Lys Ala Pro Val Thr Ile Val Ala Phe Ser
100                 105                 110                 115 gac ttt aca tgt ttg tac tgt tca caa gct tct aaa act gta caa caa     442
Asp Phe Thr Cys Leu Tyr Cys Ser Gln Ala Ser Lys Thr Val Gln Gln
                 120                 125                 130 atg ctt att gat tat aaa gat aat gta aaa tat att ttt aaa cac ttc     490
Met Leu Ile Asp Tyr Lys Asp Asn Val Lys Tyr Ile Phe Lys His Phe
             135                 140                 145 ccg ctt aaa gga cat act att tca caa caa gcg gca ata tat ttc att     538
Pro Leu Lys Gly His Thr Ile Ser Gln Gln Ala Ala Ile Tyr Phe Ile
         150                 155                 160 gct gca tct ttc caa agt aat gaa aaa gca tgg gca ctt tat gat ctt     586
Ala Ala Ser Phe Gln Ser Asn Glu Lys Ala Trp Ala Leu Tyr Asp Leu
165                 170                 175 ctt ttt caa aaa aga gat gag cta tta caa aac ggt gaa cag act ctt     634
Leu Phe Gln Lys Arg Asp Glu Leu Leu Gln Asn Gly Glu Gln Thr Leu
180                 185                 190                 195 aaa caa gca gta aaa gaa gtg gga cta gat ata aaa aag tta atg agt     682
Lys Gln Ala Val Lys Glu Val Gly Leu Asp Ile Lys Lys Leu Met Ser
                 200                 205                 210 gac ctc aac aaa gca gaa gta aac aat att ctt gga caa gac ata aaa     730
Asp Leu Asn Lys Ala Glu Val Asn Asn Ile Leu Gly Gln Asp Ile Lys
             215                 220                 225 gat gct gca caa ctt gat att agt ggt act cca tac ttt att gtt aat     778
Asp Ala Ala Gln Leu Asp Ile Ser Gly Thr Pro Tyr Phe Ile Val Asn
         230                 235                 240 aac ctt atc ctt cgt ggt gca tta cct cct gaa tta ttc aca gaa gca     826
Asn Leu Ile Leu Arg Gly Ala Leu Pro Pro Glu Leu Phe Thr Glu Ala
245                 250                 255 att aat atg gcc tta aaa aat aca aaa gaa gtg tca aca tct cca aaa     874
Ile Asn Met Ala Leu Lys Asn Thr Lys Glu Val Ser Thr Ser Pro Lys
260                 265                 270                 275 taa attctaaaag gtgtcataac tacaacacat tactatataa tgaaacctat          927
```
gctagtatat ttattacaat actt                                                                                  951

<210> SEQ ID NO 12
<211> LENGTH: 275
<212> TYPE: PRT
<213> ORGANISM: Lawsonia intracellularis

<400> SEQUENCE: 12

Met Leu Phe Ser Phe Arg Phe Ile Thr Tyr Pro Leu Ile Thr Ile Phe
1               5                   10                  15

Ile Leu Tyr Thr Cys His Asn Ala Leu Ala Ser Asn Asn Asp Ser Met
            20                  25                  30

Ile Thr Ser Glu Asn Phe Glu Ser Gln Leu Arg Leu Leu Leu His Asn
        35                  40                  45

His Pro Glu Leu Val Leu Asp Val Leu Arg Glu His Ser Glu Leu Val
    50                  55                  60

Leu Glu Ile Ala Gln Gln Gly Ser Lys Gln Arg Gln His Lys Ser Leu
65                  70                  75                  80

Ile Ala Gln Trp Lys Lys Asp Ile Thr Thr Pro Lys Asn Met His Leu
                85                  90                  95

Glu Asn Arg Pro Ile Arg Gly Asn Pro Lys Ala Pro Val Thr Ile Val
            100                 105                 110

Ala Phe Ser Asp Phe Thr Cys Leu Tyr Cys Ser Gln Ala Ser Lys Thr
        115                 120                 125

Val Gln Gln Met Leu Ile Asp Tyr Lys Asp Asn Val Lys Tyr Ile Phe
    130                 135                 140

Lys His Phe Pro Leu Lys Gly His Thr Ile Ser Gln Gln Ala Ala Ile
145                 150                 155                 160

Tyr Phe Ile Ala Ala Ser Phe Gln Ser Asn Glu Lys Ala Trp Ala Leu
                165                 170                 175

Tyr Asp Leu Leu Phe Gln Lys Arg Asp Glu Leu Leu Gln Asn Gly Glu
            180                 185                 190

Gln Thr Leu Lys Gln Ala Val Lys Glu Val Gly Leu Asp Ile Lys Lys
        195                 200                 205

Leu Met Ser Asp Leu Asn Lys Ala Glu Val Asn Asn Ile Leu Gly Gln
210                 215                 220

Asp Ile Lys Asp Ala Ala Gln Leu Asp Ile Ser Gly Thr Pro Tyr Phe
225                 230                 235                 240

Ile Val Asn Asn Leu Ile Leu Arg Gly Ala Leu Pro Pro Glu Leu Phe
                245                 250                 255

Thr Glu Ala Ile Asn Met Ala Leu Lys Asn Thr Lys Glu Val Ser Thr
            260                 265                 270

Ser Pro Lys
        275

<210> SEQ ID NO 13
<211> LENGTH: 34
<212> TYPE: DNA
<213> ORGANISM: Lawsonia

<400> SEQUENCE: 13
catgccatgg atagtaataa tgattcaatg atta                                                                        34

<210> SEQ ID NO 14
<211> LENGTH: 29
<212> TYPE: DNA

<213> ORGANISM: Lawsonia

<400> SEQUENCE: 14
cgcggatcct tattttggag atgttgaca                                29

<210> SEQ ID NO 15
<211> LENGTH: 32
<212> TYPE: DNA
<213> ORGANISM: Lawsonia

<400> SEQUENCE: 15
catgccatgg ctaaaaaatt actctttact tc                            32

<210> SEQ ID NO 16
<211> LENGTH: 29
<212> TYPE: DNA
<213> ORGANISM: Lawsonia

<400> SEQUENCE: 16
cgcggatccg aaaggccaga gggtatcca                                29

<210> SEQ ID NO 17
<211> LENGTH: 32
<212> TYPE: DNA
<213> ORGANISM: Lawsonia

<400> SEQUENCE: 17
catgccatgg cttcgatcaa tacactttc gg                             32

<210> SEQ ID NO 18
<211> LENGTH: 29
<212> TYPE: DNA
<213> ORGANISM: Lawsonia

<400> SEQUENCE: 18
cgcggatccc tgttttaaag aaagtaaag                                29

<210> SEQ ID NO 19
<211> LENGTH: 32
<212> TYPE: DNA
<213> ORGANISM: Lawsonia

<400> SEQUENCE: 19
catgccatgg ctagggttac ccaccaatca at                            32

<210> SEQ ID NO 20
<211> LENGTH: 29
<212> TYPE: DNA
<213> ORGANISM: Lawsonia

<400> SEQUENCE: 20
cgcggatcca atgtattttg ttaaattta                                29

<210> SEQ ID NO 21
<211> LENGTH: 32
<212> TYPE: DNA
<213> ORGANISM: Lawsonia

<400> SEQUENCE: 21
catgccatgg ctatttcatt aaataattca tc                            32

<210> SEQ ID NO 22
<211> LENGTH: 29

```
<212> TYPE: DNA
<213> ORGANISM: Lawsonia

<400> SEQUENCE: 22
cgcggatccc gccagaatac gctgtgttg                                29

<210> SEQ ID NO 23
<211> LENGTH: 32
<212> TYPE: DNA
<213> ORGANISM: Lawsonia

<400> SEQUENCE: 23
catgccatgg cttctttggt cattaacaac aa                            32

<210> SEQ ID NO 24
<211> LENGTH: 29
<212> TYPE: DNA
<213> ORGANISM: Laswonia

<400> SEQUENCE: 24
cgcggatccg ccactaatga gttggcttg                                29
```